(12) United States Patent
Kesten et al.

(10) Patent No.: US 10,549,076 B2
(45) Date of Patent: *Feb. 4, 2020

(54) UNCINATE PROCESS SUPPORT FOR ETHMOID INFUNDIBULUM ILLUMINATION

(71) Applicant: Acclarent, Inc., Irvine, CA (US)

(72) Inventors: Randy J. Kesten, Mountain View, CA (US); Daniel T. Harfe, Los Altos, CA (US); Eric Goldfarb, Belmont, CA (US)

(73) Assignee: Acclarent, Inc., Irvine, CA (US)

( * ) Notice: Subject to any disclaimer, the term of this patent is extended or adjusted under 35 U.S.C. 154(b) by 301 days.

This patent is subject to a terminal disclaimer.

(21) Appl. No.: 15/484,551

(22) Filed: Apr. 11, 2017

(65) Prior Publication Data

US 2017/0274192 A1    Sep. 28, 2017

Related U.S. Application Data

(63) Continuation of application No. 14/484,520, filed on Sep. 12, 2014, now Pat. No. 9,623,213, which is a
(Continued)

(51) Int. Cl.
*A61M 25/10* (2013.01)
*A61B 1/00* (2006.01)
(Continued)

(52) U.S. Cl.
CPC ... *A61M 25/10184* (2013.11); *A61B 1/00183* (2013.01); *A61B 1/233* (2013.01);
(Continued)

(58) Field of Classification Search
CPC ..... A61B 1/00183; A61B 1/233; A61B 17/24; A61B 2017/246; A61B 2090/306;
(Continued)

(56) References Cited

U.S. PATENT DOCUMENTS

| | | |
|---|---|---|
| 3,811,448 A | 5/1974 | Morton |
| 4,850,358 A | 7/1989 | Miller |
| (Continued) | | |

FOREIGN PATENT DOCUMENTS

| | | |
|---|---|---|
| EP | 1477104 | 11/2004 |
| WO | WO 95/05865 | 3/1995 |
| (Continued) | | |

OTHER PUBLICATIONS

International Search Report and Written Opinion dated Jan. 14, 2015 for Application No. PCT/US2014/018364.
(Continued)

*Primary Examiner* — Adam Marcetich
(74) *Attorney, Agent, or Firm* — Frost Brown Todd LLC

(57) ABSTRACT

A dilation apparatus comprises an elongate member and a dilation assembly that is slidable along the elongate member. The dilation assembly comprises a platform and an inflatable dilator. The platform and the elongate member cooperate to absorb inflation forces from the dilator directed toward the longitudinal axis of the elongate member, such that the dilation forces are exerted against tissue asymmetrically relative to the longitudinal axis of the elongate member. The dilation apparatus may be used to dilate the ethmoid infundibulum in a human patient. Various devices may be used to maintain the dilated state of an ethmoid infundibulum, including a wedge, a mesh, and a tether. An illuminator may be configured to reach around an uncinate process, retract the uncinate process, and then illuminate the ethmoid infundibulum to provide improved visualization of the ethmoid infundibulum.

20 Claims, 18 Drawing Sheets

Related U.S. Application Data continuation-in-part of application No. 13/832,167, filed on Mar. 15, 2013, now Pat. No. 9,615,959.

(51) Int. Cl.

| | |
|---|---|
| *A61B 1/233* | (2006.01) |
| *A61B 17/24* | (2006.01) |
| *A61M 25/09* | (2006.01) |
| *A61M 29/02* | (2006.01) |
| *A61F 5/08* | (2006.01) |
| *A61M 25/01* | (2006.01) |
| *A61M 25/00* | (2006.01) |
| *A61M 25/06* | (2006.01) |
| *A61B 90/30* | (2016.01) |

(52) U.S. Cl.
CPC ............... *A61B 17/24* (2013.01); *A61F 5/08* (2013.01); *A61M 25/09* (2013.01); *A61M 29/02* (2013.01); *A61B 2017/246* (2013.01); *A61B 2090/306* (2016.02); *A61M 25/0041* (2013.01); *A61M 25/1002* (2013.01); *A61M 2025/0183* (2013.01); *A61M 2025/0681* (2013.01); *A61M 2025/0915* (2013.01); *A61M 2025/09175* (2013.01); *A61M 2025/1084* (2013.01); *A61M 2029/025* (2013.01); *A61M 2210/0681* (2013.01)

(58) Field of Classification Search
CPC ............. A61F 5/08; A61M 2025/0183; A61M 2025/0681; A61M 2025/0915; A61M 2025/09175; A61M 2025/1084; A61M 2029/025; A61M 2210/0681; A61M 25/0041; A61M 25/09; A61M 25/1002; A61M 25/10184; A61M 29/02
See application file for complete search history.

(56) References Cited

U.S. PATENT DOCUMENTS

| | | | |
|---|---|---|---|
| 5,024,658 A | 6/1991 | Kozlov et al. | |
| 5,327,891 A * | 7/1994 | Rammler | A61B 8/0833 |
| | | | 600/435 |
| 5,578,009 A | 11/1996 | Kraus et al. | |
| 5,669,880 A | 9/1997 | Solar | |
| 5,718,684 A | 2/1998 | Gupta | |
| 5,738,667 A * | 4/1998 | Solar | A61F 2/95 |
| | | | 604/103.04 |
| 5,836,957 A | 11/1998 | Schulz et al. | |
| 5,882,334 A | 3/1999 | Sepetka et al. | |
| 6,245,040 B1 | 6/2001 | Inderbitzen et al. | |
| 6,447,501 B1 | 9/2002 | Solar et al. | |
| 6,780,199 B2 | 8/2004 | Solar et al. | |
| 6,837,864 B1 * | 1/2005 | Bertolero | A61M 25/003 |
| | | | 604/4.01 |
| 8,657,846 B2 | 2/2014 | Keith et al. | |
| 8,672,990 B2 | 3/2014 | Holman et al. | |
| 8,979,888 B2 | 3/2015 | Morriss et al. | |
| 2002/0010489 A1 | 1/2002 | Grayzel et al. | |
| 2002/0032457 A1 | 3/2002 | Sirhan et al. | |
| 2002/0147487 A1 * | 10/2002 | Sundquist | A61N 1/056 |
| | | | 607/122 |
| 2003/0018376 A1 | 1/2003 | Solar et al. | |
| 2003/0171642 A1 * | 9/2003 | Schock | A61M 25/09 |
| | | | 600/18 |
| 2003/0195546 A1 | 10/2003 | Solar | |
| 2004/0167439 A1 * | 8/2004 | Sharrow | A61M 25/09 |
| | | | 600/585 |
| 2005/0159645 A1 | 7/2005 | Bertolero et al. | |
| 2006/0079836 A1 * | 4/2006 | Holman | A61M 25/10 |
| | | | 604/96.01 |
| 2006/0264784 A1 * | 11/2006 | Lupton | A61M 25/09 |
| | | | 600/585 |
| 2007/0078396 A1 | 4/2007 | Feeley et al. | |
| 2007/0244501 A1 | 10/2007 | Horn | |
| 2008/0009927 A1 | 1/2008 | Vilims | |
| 2008/0082049 A1 * | 4/2008 | Evans | A61M 25/09041 |
| | | | 604/164.13 |
| 2008/0172033 A1 | 7/2008 | Keith et al. | |
| 2008/0194991 A1 * | 8/2008 | Teague | A61M 25/09 |
| | | | 600/585 |
| 2008/0200944 A1 | 8/2008 | Hardert | |
| 2009/0088685 A1 | 4/2009 | Kugler et al. | |
| 2009/0171284 A1 | 7/2009 | Burke et al. | |
| 2009/0318947 A1 | 12/2009 | Garcia et al. | |
| 2010/0030031 A1 | 2/2010 | Goldfarb et al. | |
| 2010/0076269 A1 | 3/2010 | Makower et al. | |
| 2011/0004057 A1 | 1/2011 | Goldfarb et al. | |
| 2011/0082488 A1 | 4/2011 | Niazi | |
| 2011/0224606 A1 | 9/2011 | Shome et al. | |
| 2012/0059401 A1 | 3/2012 | Konstantino et al. | |
| 2012/0071856 A1 | 3/2012 | Goldfarb et al. | |
| 2012/0078118 A1 | 3/2012 | Jenkins et al. | |
| 2012/0109177 A1 | 5/2012 | Ulmer | |
| 2013/0165774 A1 * | 6/2013 | Nocca | A61F 5/0083 |
| | | | 600/431 |
| 2013/0204184 A1 | 8/2013 | Weber et al. | |
| 2013/0317409 A1 | 11/2013 | Cully et al. | |
| 2014/0275804 A1 | 9/2014 | Kesten et al. | |
| 2014/0276408 A1 | 9/2014 | Abbate | |

FOREIGN PATENT DOCUMENTS

| | | |
|---|---|---|
| WO | WO 2011/106735 | 9/2011 |
| WO | WO 2013/066566 | 5/2013 |
| WO | WO 2013/119735 | 8/2013 |
| WO | WO 2014/149431 | 9/2014 |

OTHER PUBLICATIONS

International Preliminary Report on Patentability dated Sep. 15, 2015 for Application No. PCT/US2014/018364.
International Search Report and Written Opinion dated Dec. 7, 2015 for Application No. PCT/US2015/049719, 17 pages.
U.S. Appl. No. 14/484,520, filed Sep. 12, 2014.
U.S. Appl. No. 13/832,167, filed Mar. 15, 2013.
U.S. Appl. No. 61/725,523, filed Nov. 13, 2012.

* cited by examiner

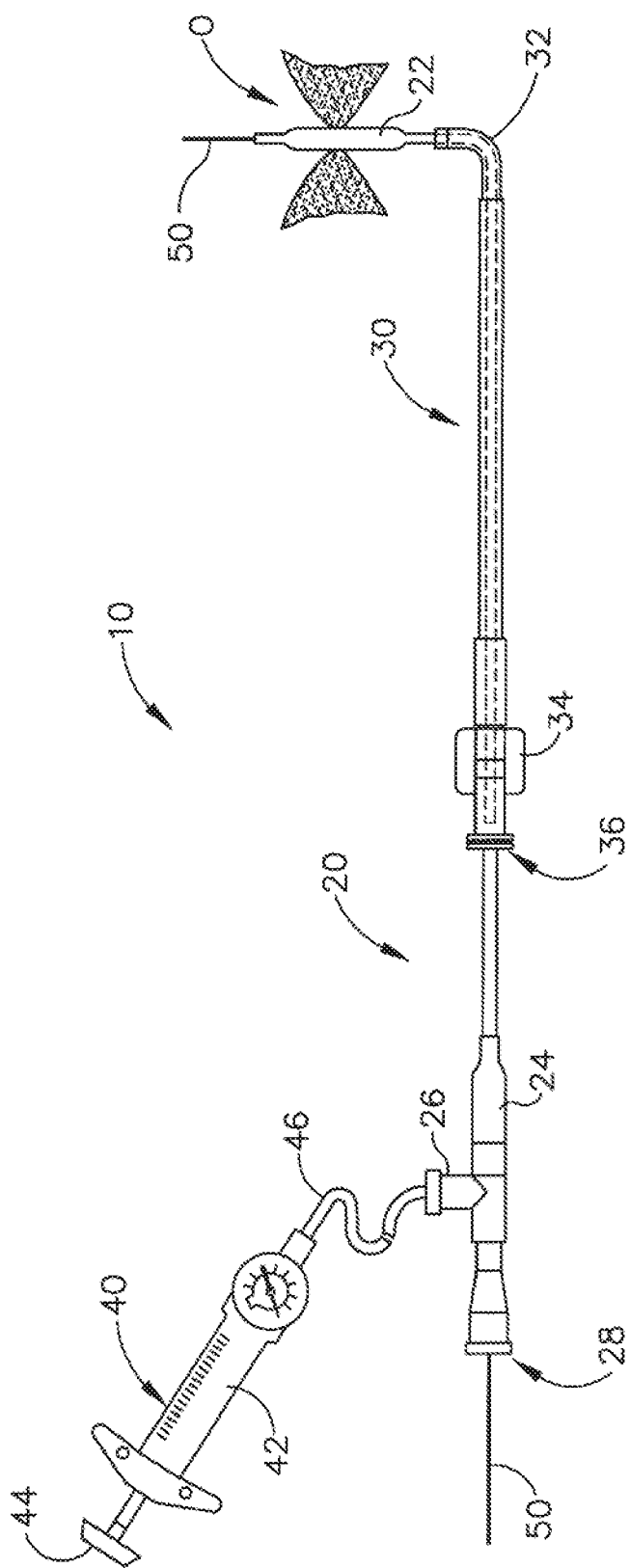

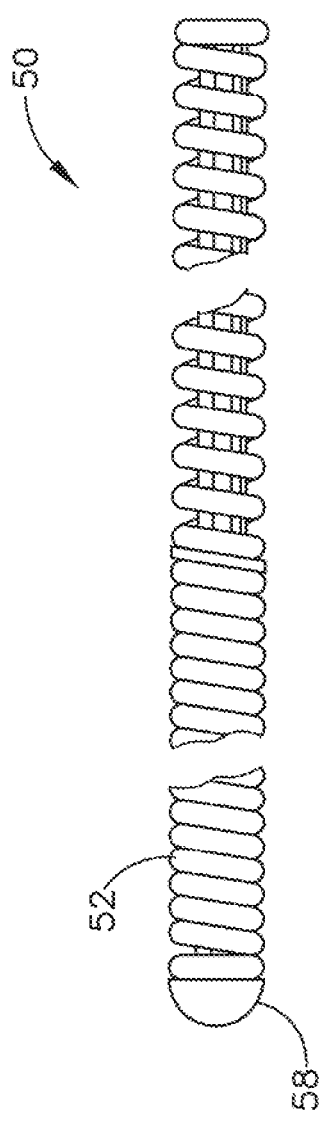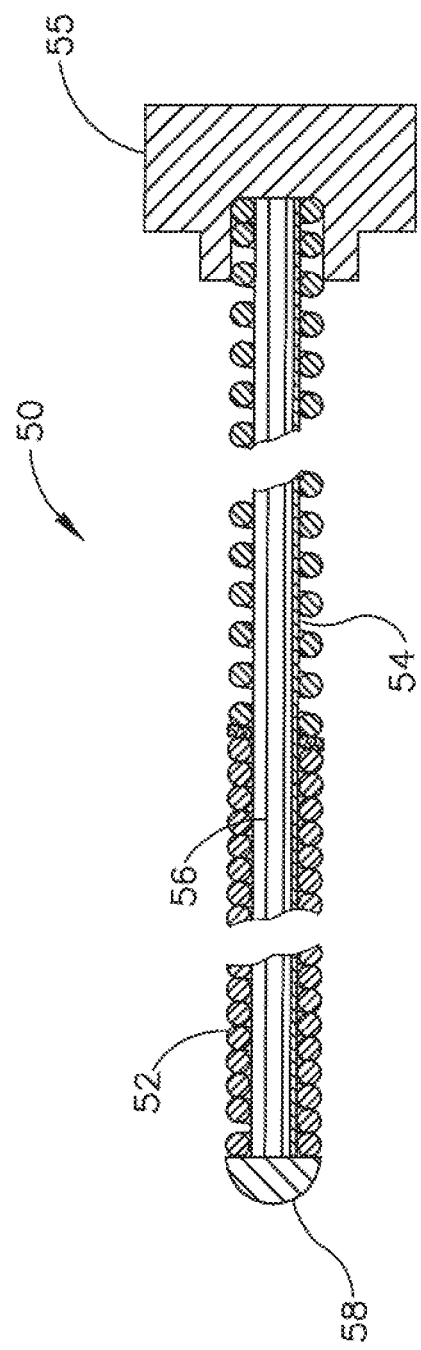

UNCINATE PROCESS SUPPORT FOR ETHMOID INFUNDIBULUM ILLUMINATION

PRIORITY

This application is a continuation of U.S. patent application Ser. No. 14/484,520, entitled "Uncinate Process Support for Ethmoid Infundibulum Illumination," filed Sep. 12, 2014, now U.S. Pat. No. 9,623,213, issued Apr. 18, 2017, which is a continuation-in-part of U.S. patent application Ser. No. 13/832,167, entitled "Uncinate Process Support for Ethmoid Infundibulum Illumination," filed Mar. 15, 2013, now U.S. Pat. No. 9,615,959, issued Apr. 11, 2017, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now U.S. Pat. No. 9,155,492, issued Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

While several instruments and procedures have been made and used for the ear, nose, and throat, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 1 depicts a side elevational view of an exemplary dilation catheter system:

FIG. 2 depicts a side elevational view of an exemplary illuminating guidewire suitable for use with the dilation catheter system of FIG. 1;

FIG. 3 depicts a side cross-sectional view of the illuminating guidewire of FIG. 2;

Figure 4:
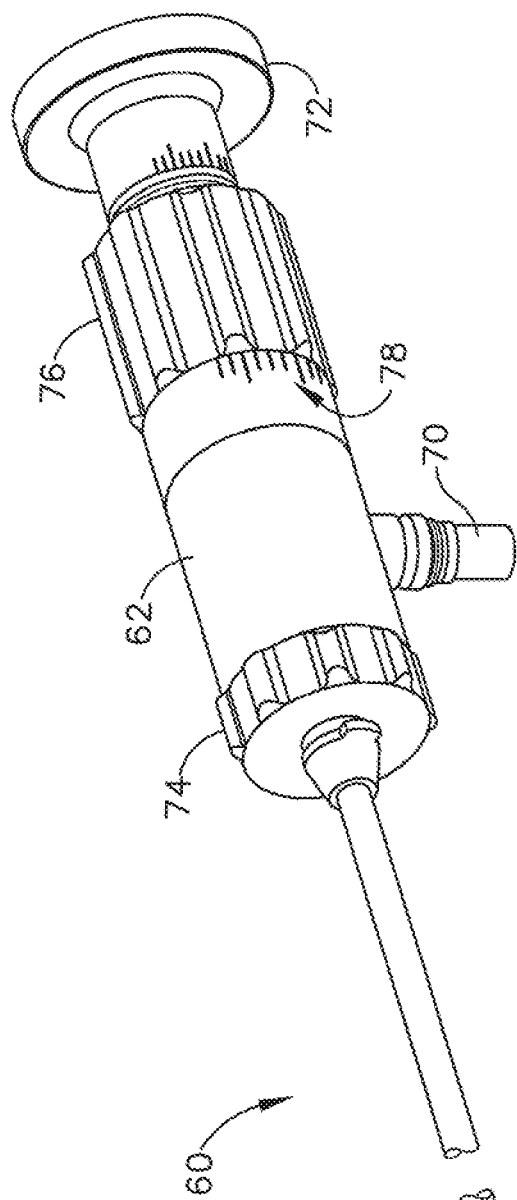
FIG. 4 depicts a perspective view of an exemplary endoscope suitable for use with the dilation catheter system of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

The distal end of dilation catheter (20) includes an inflatable dilator (22). The proximal end of dilation catheter (20) includes a grip (24), which has a lateral port (26) and an open proximal end (28). Dilation catheter (20) includes a first lumen (not shown) that provides fluid communication between lateral port (26) and the interior of dilator (22). Dilator catheter (20) also includes a second lumen (not shown) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

Guide catheter (30) of the present example includes a bent distal end (32) and a grip (34) at its proximal end. Grip (34) has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. In some versions, inflator (40) is configured in accordance with at least some of the teachings of U.S. Pat. App. No. 61/725,523, entitled "Inflator for Dilation of Anatomical Passageway," filed Nov. 13, 2012, the disclosure of which is incorporated by reference herein. Other suitable forms that inflator (40) may take will be apparent to those of ordinary skill in the art in view of the teachings herein.

As best seen in FIGS. 2-3, guidewire (50) of the present example comprises a coil (52) positioned about a core wire (54). An illumination wire (56) extends along the interior of core wire (54) and terminates in an atraumatic lens (58). A connector (55) at the proximal end of guidewire (50) enables optical coupling between illumination wire (56) and a light source (not shown). Illumination wire (56) may comprise one or more optical fibers. Lens (58) is configured to project light when illumination wire (56) is illuminated by the light source, such that illumination wire (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, now U.S. Pat. No. 9,155,492, issued Oct. 13, 2015, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as a sinus ostium (O). Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium (O) to be dilated. This positioning of guide catheter (30) may be performed under visualization provided by an endoscope such as endoscope (60) described below. After guide catheter (30) has been positioned, the operator may advance guidewire (50) distally through guide catheter (30) such that a distal portion of the guidewire (50) passes through the sinus ostium (O) and into the sinus cavity. The operator may illuminate illumination wire (56) and lens (58), which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (O) (or some other targeted anatomical passageway). After dilator (22) has been positioned within the ostium (O), dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

II. Overview of Exemplary Endoscope

Figure 5:
FIG. 5 depicts a side elevational view of the distal end of the endoscope of FIG. 5, showing an exemplary range of viewing angles.

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein.

III. Exemplary Dilation of the Ethmoid Infundibulum

Figure 6:
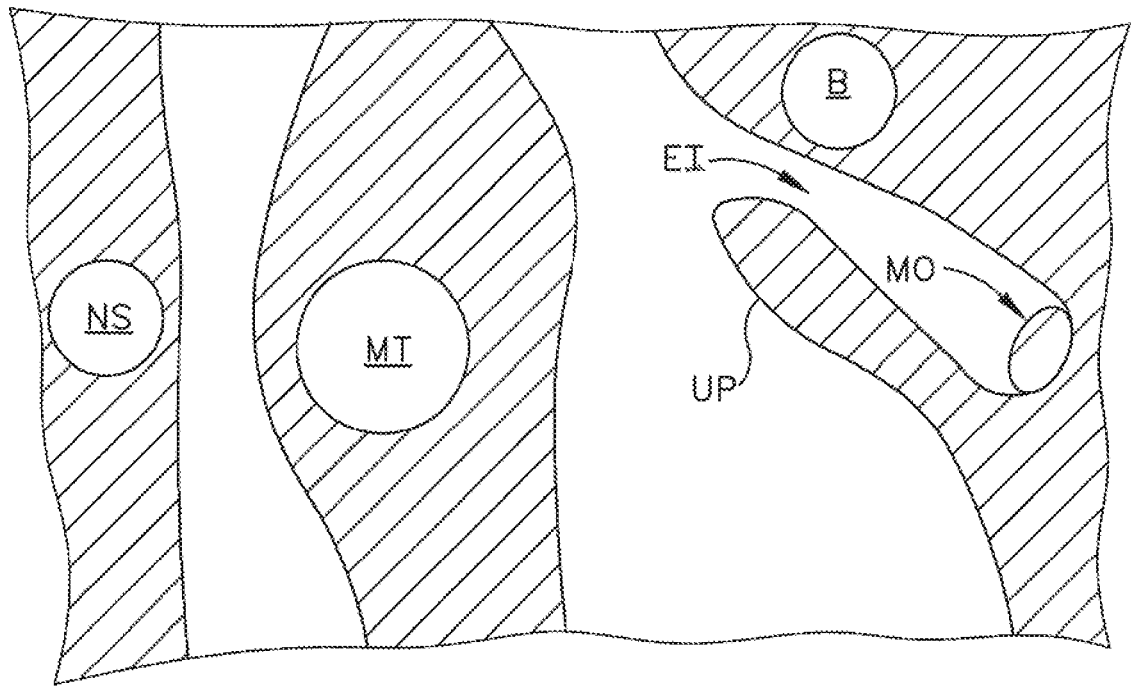
FIG. 6 depicts a coronal cross-sectional view of a portion of a nasal cavity, showing portions of the nasal septum, middle turbinate, ethmoid bulla, uncinate process, and ostium of a maxillary sinus.

FIG. 6 shows a coronal cross-sectional view of a left portion of a patient's nasal cavity. In particular, FIG. 6 shows the nasal septum (NS), the middle turbinate (MT) lateral to the nasal septum (NS), and the uncinate process (UP) and ethmoid bulla (B) lateral to the middle turbinate (MT). The uncinate process (UP) and the ethmoid bulla (B) together define the ethmoid infundibulum (EI), which is a transition space leading to the maxillary ostium (MO). The maxillary ostium (MO) provides a passageway between the ethmoid infundibulum (EI) and the maxillary sinus (not shown).

In some instances, it may be desirable to use dilation catheter system (10) to dilate the maxillary ostium (MO) of a patient or to otherwise reach the maxillary ostium (MO). However, the uncinate process (UP) may make it difficult to visualize and reach the maxillary ostium (MO). It may therefore be desirable to at least temporarily move the uncinate process (UP), to thereby dilate the ethmoid infundibulum (EI) and improve access to (and visualization of) the maxillary ostium (MO). Since the uncinate process (UP) is a fragile structure, a balloon may be used to gently move the uncinate process (UP) since a balloon may provide a relatively large surface area contact. While examples herein refer to dilating the ethmoid infundibulum (EI) in order to improve access to the maxillary ostium (MO), to thereby use dilation catheter system (10) to dilate the maxillary ostium (MO), it should be understood that there may be other reasons to dilate the ethmoid infundibulum (EI). By way of example only, dilating the ethmoid infundibulum (EI) may simply provide patency to improve flow of air/mucus/etc. into and out of the maxillary sinus. Dilating the ethmoid infundibulum (EI) may also facilitate the removal of obstructions from within the ethmoid infundibulum (EI). Other potential reasons for dilating the ethmoid infundibulum (EI) will be apparent to those of ordinary skill in the art in view of the teachings herein.

Figure 7:
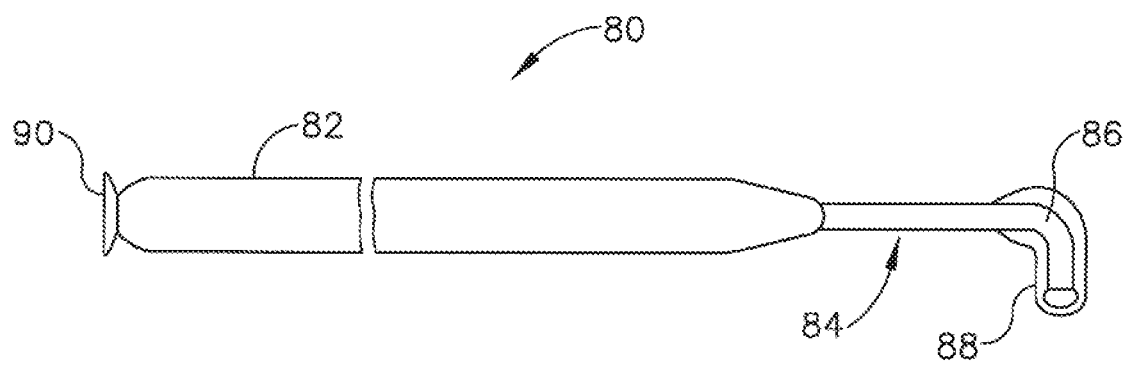
FIG. 7 depicts a side elevational view of an exemplary infundibular probe and dilator.

FIG. 7 shows an exemplary dilation instrument (80) that may be used to gently move the uncinate process (UP), to thereby dilate the ethmoid infundibulum (EI) and improve access to (and visualization of) the maxillary ostium (MO). Dilation instrument (80) of this example comprises a handpiece (82), and a shaft (84) extending distally from handpiece (82). At least a portion of shaft (84) may be malleable or semi-rigid. Shaft (84) includes a curved probe tip (86). The curvature and length of probe tip (86) are selected to enable curved probe tip (86) to be positioned around the uncinate process (UP) and into the ethmoid infundibulum (EI). A dilator (88) is disposed about curved probe tip (86) and is operable to transition between an inflated state and a non-inflated state. Dilator (88) is thus similar to dilator (22) described above. However, in the present example dilator (88) is inflatable to a larger cross-sectional area than dilator (22), since dilator (22) is configured to dilate smaller passageways (e.g., sinus ostia) than dilator (88). Dilator (88) is formed of a compliant material such that its shape will conform to the shape of anatomical structures that dilator (88) bears against when in an inflated state. By way of example only, dilator (88) may be formed of a thermoplastic elastomer such as urethane, polyether block amide such as PEBAX® (by Arkema of Paris, France), Hytrel® (by E. I. du Pont de Nemours and Company of Wilmington, Del.), and/or any other suitable material(s). Dilator (88) is in fluid communication with a port (90) located at the proximal end of handpiece (82). Port (90) is configured to couple with a fluid source (e.g., a source of saline) via any suitable means. By way of example only, port (90) may comprise a leur connector.

Figure 8A:
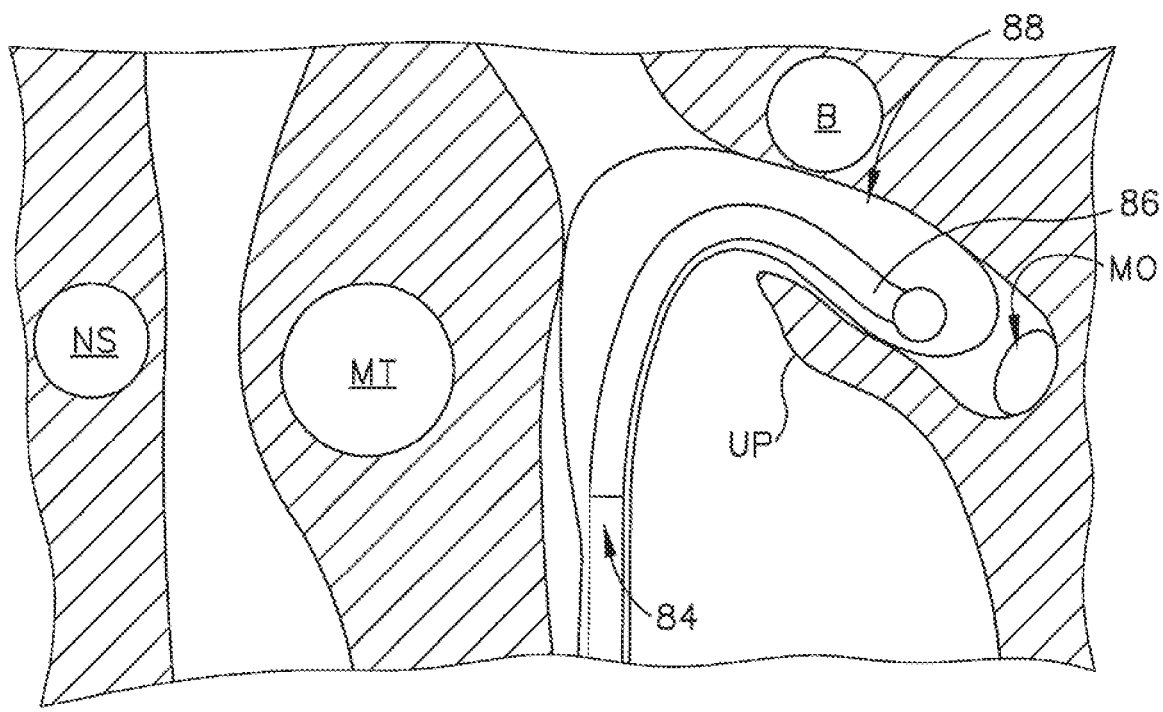
FIG. 8A depicts a coronal cross-sectional view of the portion of the nasal cavity depicted in FIG. 6, with the probe positioned in the infundibular space and with the dilator in a dilated state.

In an exemplary use, dilation instrument (80) is inserted into the patient's nasal cavity and curved probe tip (86) is navigated around the uncinate process (UP) into the ethmoid infundibulum (EI). This may be accomplished using direct vision, endoscope (60) described above, some other kind of endoscope, or some other means of visualization. Once curved probe tip (86) is appropriately positioned, fluid is communicated to dilator (88) via port (90), such that dilator (88) transitions to an inflated state as shown in FIG. 8A. As dilator (88) inflates, dilator (88) dilates the ethmoid infundibulum (EI). It should be understood that one or more of the anatomical structures around the ethmoid infundibulum (EI) may be moved by dilator (88) to provide this dilation. In some instances, inflating dilator (88) moves the uncinate process (UP) inferiorly and/or anteriorly. In addition or in the alternative, inflating dilator (88) may move the middle turbinate (MT) medially. In addition or in the alternative, inflating dilator (88) may move ethmoid bulla (B) superiorly and/or posteriorly. Because dilator (88) is formed of a compliant material, it conforms to the shape of the uncinate process (UP), the middle turbinate (MT), and the ethmoid bulla (B), such that the contact between dilator (88) and the uncinate process (UP), the middle turbinate (MT), and the ethmoid bulla (B) is over a maximum surface area. This may reduce the risk of trauma to the uncinate process (UP), the middle turbinate (MT), and the ethmoid bulla (B) due to expansion of dilator (88).

Figure 8B:
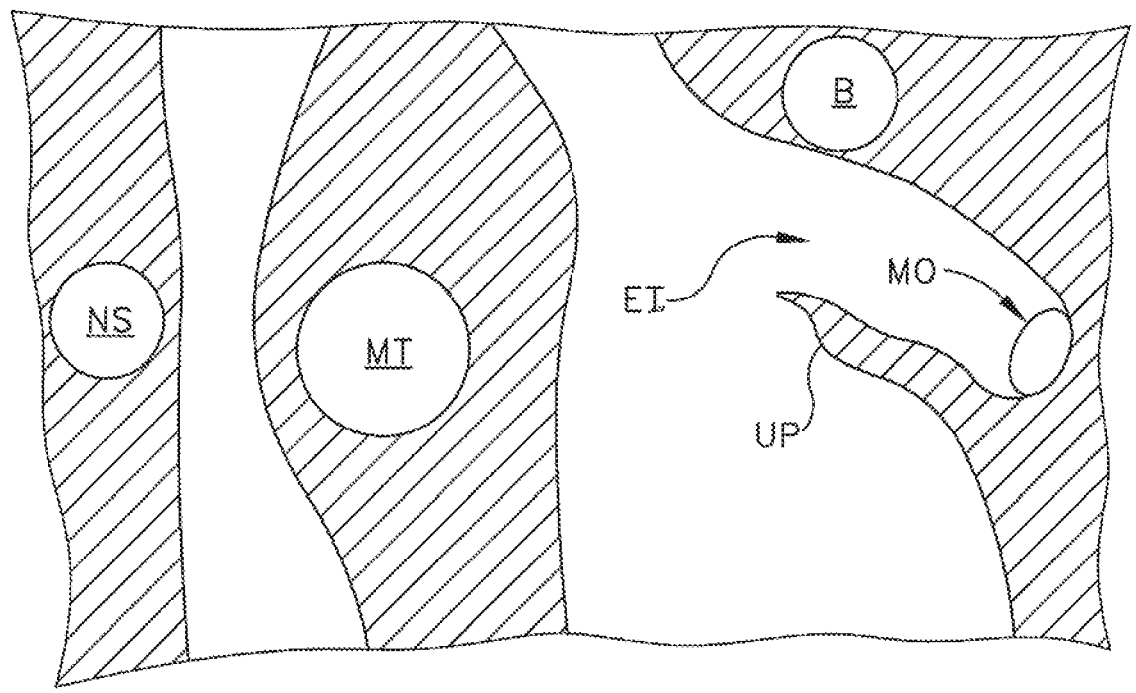
FIG. 8B depicts a coronal cross-sectional view of the portion of the nasal cavity depicted in FIG. 6, with the uncinate process remodeled to dilate the infundibular space.

In the present example, after dilator (88) dilates the ethmoid infundibulum (EI), the result is shown in FIG. 8B, where the passageway provided by the ethmoid infundibulum (EI) is significantly larger than the pre-dilation passageway shown in FIG. 6. This larger, dilated passageway provided by the ethmoid infundibulum (EI) enhances access to and visualization of the maxillary ostium (MO). In some instances, an additional device may be installed to maintain the dilation of the ethmoid infundibulum (EI). Various examples of such devices will be described in greater detail below, while others will be apparent to those of ordinary skill in the art in view of the teachings herein.

It should be understood that some versions of dilation instrument (80) may be inserted through guide catheter (30) or a variation thereof. Furthermore, dilation instrument (80) may be constructed as a variation of dilator catheter (20) (e.g., having a dilator (88) that is different from dilator (22)). Dilation instrument (80) may also be configured to slide along a guidewire such as guidewire (50). Alternatively, dilation instrument (80) may be used without any kind of guide catheter (30) or guidewire (50). In addition, dilation instrument (80) may be constructed and operable in accordance with at least some of the teachings of U.S. Pub. No. 2010/0030113, entitled "Paranasal Ostium Finder Devices and Methods," published Feb. 4, 2010, now U.S. Pat. No. 8,979,888, issued Mar. 17, 2015, the disclosure of which is incorporated by reference herein.

FIGS. 9A-10B show another exemplary dilation instrument (100) that may be used to dilate nasal and paranasal structures. Dilation instrument (100) of the present example comprises a hollow rail (110) and a dilator assembly (120) that translates along rail (110). The exterior of rail (110) presents a pair of inwardly extending tracks (118) along the length of rail (110). Tracks (118) are configured to enable translation of dilator assembly (120) along rail (110) as will be described in greater detail below. Rail (110) includes a radiused curved region (112) and a distally narrowing tapered region (114) distal to curved region (112). In some instances, the taper of tapered region (114) extends along at least part of the length of curved region (112). A ball tip (116) is positioned at the distal end of tapered region (114). The curvature of curved region (112) is selected to facilitate positioning of the distal end of dilation instrument (100) in a paranasal passageway (e.g., in the ethmoid infundibulum (EI), etc.). The configuration of ball tip (116) is atraumatic to reduce the risk of inadvertently damaging tissue while navigating dilation instrument (100) into position. It should also be understood that ball tip (116) may be used for atraumatic exploration of areas such as the frontal recess in a patient. The frontal recess may have several pathways, some of which are "dead ends" known as terminal recesses. Ball tip (116) may allow the operator to assess whether a recess leads to other structures or is a terminal recess.

Figure 10A:
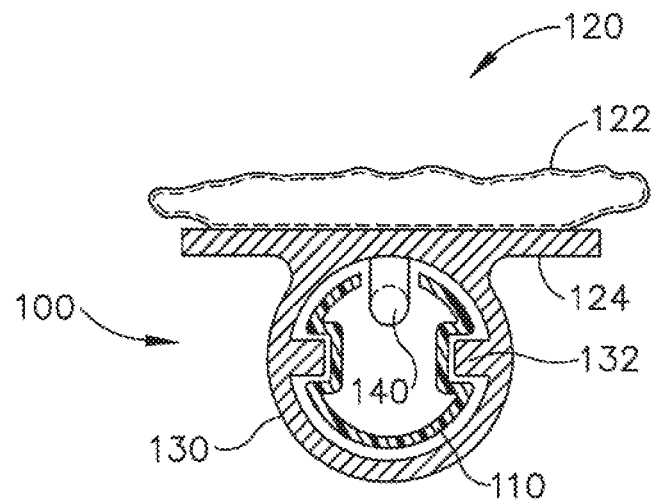
FIG. 10A depicts a cross-sectional view of the dilator device of FIG. 9A, taken along line 10A-10A of FIG. 9A.
Figure 10B:
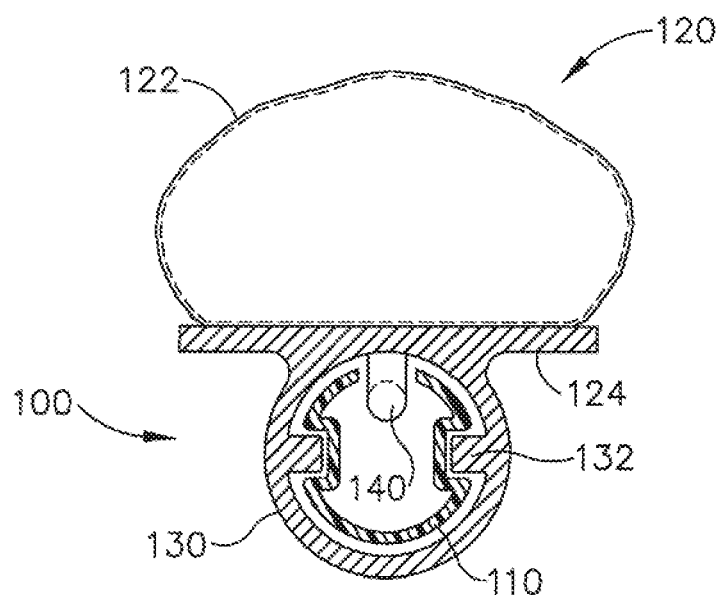
FIG. 10B depicts a cross-sectional view of the dilator device of FIG. 9A, taken along line 10B-10B of FIG. 9B

Dilator assembly (120) of the present example comprises an inflatable dilator (122) secured to a sled platform (124). In the present example, dilator (122) and sled platform (124) are located at an angular position about the longitudinal axis of rail (110) such that dilator (122) and sled platform (124) are on the inside of the curve defined by curved region (112). In some other versions, dilator (122) and sled platform (124) are oriented such that dilator (122) and sled platform (124) are on the outside of the curve defined by curved region (112). Alternatively, dilator (122) and sled platform (124) may be oriented such that dilator (122) and sled platform (124) are on a lateral side (e.g., 90 degrees from the inside/outside) of the curve defined by curved region (112). Of course, any other orientation may be used. Sled platform (124) includes a pair of guide blocks (130), though it should be understood that any suitable number of guide blocks (130) may be used. As shown in FIGS. 10A-10B, guide blocks (130) include integral male key elements (132) that project inwardly and are received in tracks (118). The disposition of key elements (132) in tracks (118) provides angular stability for platform (124) about the longitudinal axis of rail (110); yet enable platform (124) to freely slide longitudinally along rail (110). Other suitable relationships between guide blocks (130) and rail (110) will be apparent to those of ordinary skill in the art in view of the teachings herein. For instance, while guide blocks (130) are positioned on the exterior of rail (110) in the present example, it should be understood that rail (110) and guide blocks (130) may be readily modified to position guide blocks (130) within the interior of rail (110).

Dilator (122) is in fluid communication with a conduit (140), which extends through the hollow interior of rail (110). Dilator (122) may be formed of a compliant material just like dilator (88) described above. In some versions, a distal portion of conduit (140) bends transversely and passes through platform (124) to reach conduit (140). In some other versions, the distal end of conduit (140) includes an angled fitting that couples conduit (140) with dilator (122). Rail (110) defines a longitudinally extending slot that enables conduit (140) or the fitting to pass from the interior of rail (110) to platform (124). Conduit (140) translates with dilator assembly (120) as dilator assembly (120) translates along rail (110). It should be understood that a variety of features may be used to drive translation of dilator assembly (120) along rail (110). By way of example only, platform (124) may be secured to a drive tube that is slidably disposed about the exterior of rail (110), such that platform (124) may be translated by translating the drive tube relative to rail (110). As yet another merely illustrative example, platform (124) may be driven by a push/pull cable feature. Other suitable ways in which dilator assembly (120) may be translated along rail (110) will be apparent to those of ordinary skill in the art in view of the teachings herein.

Figure 9A:
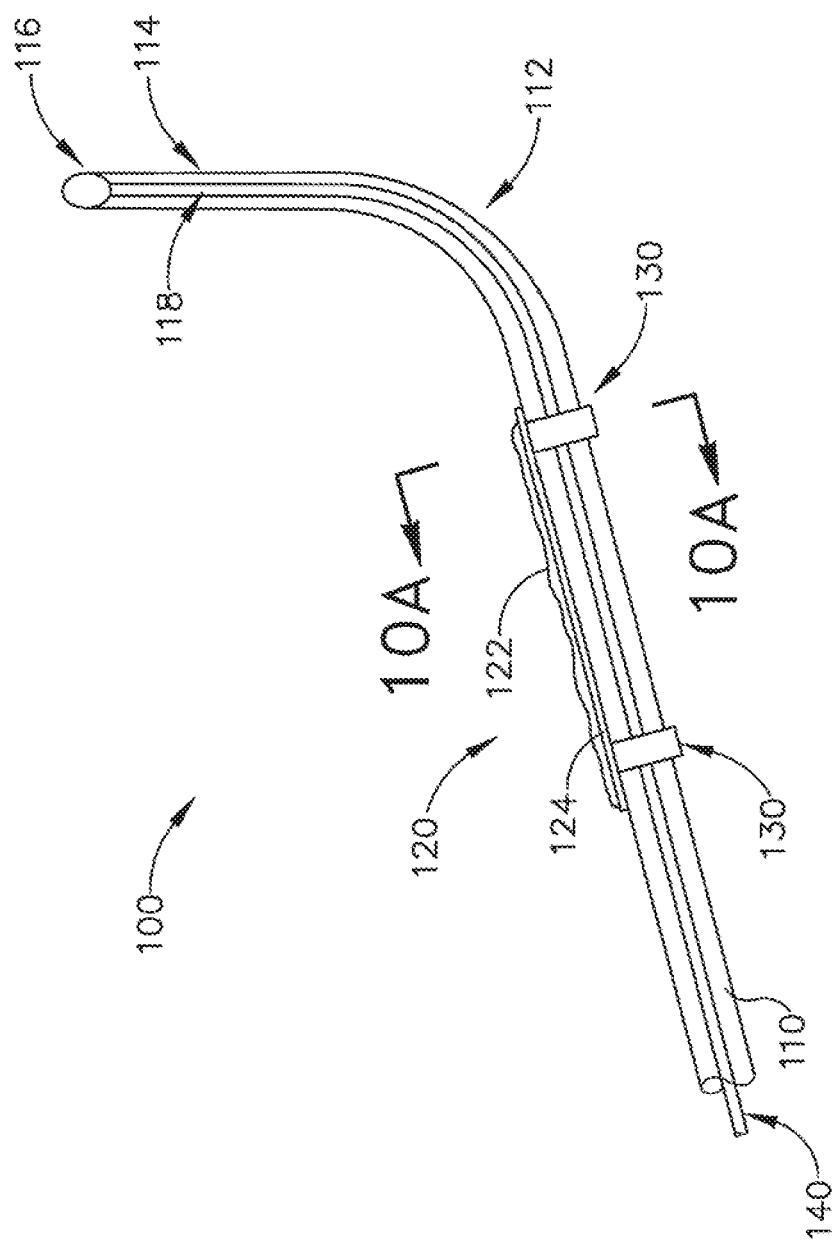
FIG. 9A depicts a side elevational view of an exemplary dilator device with a single sided balloon, with the balloon in a retracted and non-inflated state.

In an exemplary use, dilation instrument (100) is initially positioned such that tapered region (114) is located within the desired anatomical region while dilator assembly (120) is in the retracted position and non-inflated state shown in FIGS. 9A and 10A. By way of example only, dilation instrument (100) may be positioned such that tip (116) is located within the ethmoid infundibulum (EI), just medial to the maxillary ostium (MO), with curved region (112) reaching around the uncinate process (UP). Then, dilator assembly (120) is advanced distally along rail (110) until dilator (122) is positioned adjacent to the uncinate process (UP). Platform (124) is compliant enough to traverse curved region (112) while remaining engaged with rail (110) and without deforming rail (110) during such traversal. Some versions of platform (124) may include transversely extending ribs or other reinforcement features that enable such deformation without promoting deformation of platform (124) about the longitudinal axis of rail (110).

Figure 9B:
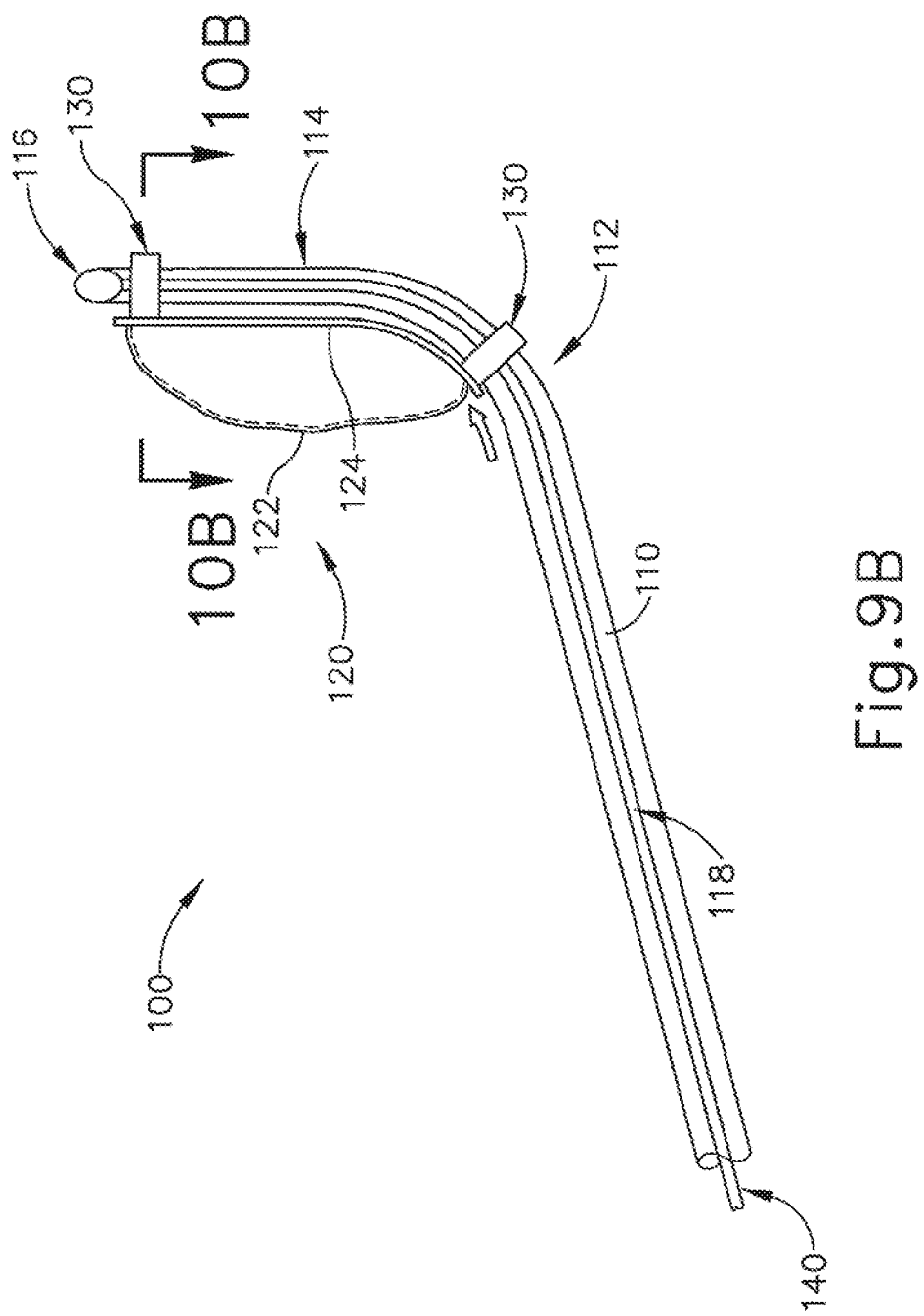
FIG. 9B depicts a side elevational view of the dilator device of FIG. 9A, with the balloon in an extended and inflated state.

After dilator assembly (120) has been advanced to a suitable distal position, fluid (e.g., saline) is then communicated through conduit (140) to inflate dilator (122) to the inflated state shown in FIGS. 9B and 10B. The expansion of dilator (122) drives the uncinate process (UP) medially and/or inferiorly, thereby dilating the ethmoid infundibulum (EI). Due to the general rigidity of rail (110) and the presence of platform (124), the only forces exerted on the patient's anatomy by inflation of dilator (122) are on the uncinate process (UP). In other words, the rigidity of rail (110) and platform (124) provides a mechanical ground that absorbs forces exerted by dilator (122) toward the ethmoid bulla (B) and the middle turbinate (MT), such that neither dilator (122) nor rail (110) bears against the ethmoid bulla (B) or the middle turbinate (MT) during inflation of dilator (122). Platform (124) thus constrains expansion of dilator (122) to only a restricted angular range (i.e., less than 360°) about the longitudinal axis of rail (100). While at least a portion of dilation instrument (100) may incidentally contact the ethmoid bulla (B) or the middle turbinate (MT) during inflation of dilator (122), those anatomical structures are not moved or remodeled by inflation of dilator (122). The forces exerted on the patient's anatomy by the inflation of dilator are thus asymmetric relative to the longitudinal axis of rail (110). After dilator (122) has been inflated to dilate the ethmoid infundibulum (EI), the fluid may be removed from dilator (122) and dilation instrument (100) may be removed from the patient. In some instances, dilation assembly (120) is retracted to a proximal position along rail (110) before rail (110) is pulled out of the patient. In some other instances, rail (110) is pulled out of the patient while dilation assembly (120) remains at a distal position along rail (110).

As noted above, dilation instrument (100) may be used in various other procedures and in various other parts of a patient's anatomy. By way of example only, dilation instrument (100) may be used to dilate the frontal recess (FR) that extends between the ethmoid infundibulum (EI) or adjacent spaces and the frontal paranasal sinus. While dilation instrument (100) is discussed herein in the context of dilating the frontal recess (FR), it should be understood that dilation instrument (100) and variations thereof may be readily used in various other procedures and locations. By way of example only, dilation instrument (100) may be used to dilate structures within the frontal recess, which is the passageway that courses past the ethmoid bulla (B) and up to the frontal sinus. Pneumatized air cells may form part of the boundaries of the frontal recess, such that it may be advantageous to be able to perform selective dilatation in that area so as to choose which of these cells to apply force to. In particular, dilation instrument (100) of the present example allows for selective remodeling of an agger nasi air cell (typically found anterior to the frontal recess (FR)) while not applying force to a suprabullar air cell (which typically lies posterior to the frontal recess (FR)). Alternatively, with the orientation of dilator assembly (120) or dilation-constraining element rotated approximately 180 degrees about the longitudinal axis of rail (110), a suprabullar air cell can be selectively remodeled while not applying force to the agger nasi cell. Other procedures and locations in which dilation instrument (100) may be used will be apparent to those of ordinary skill in the art in view of the teachings herein.

In addition to having dilator assembly (120) positioned at any suitable angular orientation about the longitudinal axis of rail (110), it should be understood that dilator (122) may be advanced to (and dilated at) any suitable location along the length of rail (110). In other words, in some uses dilator assembly (120) stops advancing at curved region (112) or proximal to curved region (112), with dilator (122) then being inflated at that point. In some alternative versions of dilation instrument (100), dilator assembly (120) does not translate along rail (110) and is simply fixed in position at the distal end of rail (110). Various suitable ways in which dilation instrument (100) may be configured and used will be apparent to those of ordinary skill in the art in view of the teachings herein.

FIGS. 11-16 show another exemplary dilation instrument (700) that may be used to dilate nasal and paranasal structures. By way of example only, dilation instrument (700) may be used in the same procedures and parts of a patient's anatomy as identified above with respect to dilation instrument (100). Other suitable same procedures and parts of a patient's anatomy where dilation instrument (700) may be used will be apparent to those of ordinary skill in the art in view of the teachings herein. Dilation instrument (700) of the present example comprises a handle (710), a rigid guide catheter (720), a guidewire (730), and a dilation catheter (740). Handle (710) is provided so that a surgeon or other operator can controllably position dilation instrument (700) and apply grounding forces to dilation instrument (700) in order to counter forces that are encountered during dilation and to thus maintain a stable position of dilation instrument (700) relative to the head of the patient. Handle (710) comprises a plurality of slidable actuators (712) and a plurality of laterally extending gripping members (714). Actuators (712) are configured to slide along the body of handle (710) to permit a user to independently advance guidewire (730), dilation catheter (740), and/or other components relative to handle (710). Gripping members (714) are configured to fit between and adjacent to a user's fingers to thereby permit a user to firmly grasp handle (710) with a single hand. Alternatively, handle (710) may have any other suitable configuration. For instance, in some other versions, handle (710) may be configured similarly to dilation catheter system (10) described above, where various functional components also serve as a grip for an operator. Other suitable forms that handle (710) may take will be apparent to those of ordinary skill in the art in view of the teachings herein.

Guide catheter (720) extends distally from handle (720). In the present example, guide catheter (720) is rigid, though in some other versions at least a portion of guide catheter (720) may be flexible or semi-rigid. Guide catheter (720) has a lumen (not shown) extending axially therethrough with an open distal end (722). As will be described in greater detail below, guidewire (730) may be slidably disposed within the lumen of guide catheter (720) such that the operator may advance guidewire (730) axially through open distal end (722). In the present example, guide catheter (720) comprises a curved portion (724) near open distal end (722) of guide catheter (720). In some versions, curved portion (724) may be more or less curved, or omitted entirely, with such a curve being adapted for dilation of the drainage pathway of a particular paranasal sinus. By way of example only, a set of instruments (700) may have guide catheters (720) with curved portions (724) presenting different curvatures, such that the operator may select a particular instrument (700) from the set with a curved portions (724) having a curvature that is particularly suited for the anatomical location in which instrument (700) will be used. Various suitable curvatures that curved portion (724) may have will be apparent to those of ordinary skill in the art in view of the teachings herein.

As described above, guidewire (730) is slidably disposed within the lumen of guide catheter (720). Guidewire (730), like guidewire (50) discussed above, may have an illuminating tip such that guidewire (730) may provide transillumination through regions of a patient's head. In addition or in the alternative, guidewire (730) may include one or more electromagnetic tracking features, a distal camera assembly, a distal ultrasonic transducer, and/or any other suitable feature(s), including combinations thereof. In the present example, the distal end of guidewire (730) comprises a ball tip (732). As will be described in greater detail below, ball tip (732) may enable guidewire (730) to be used to like a conventional "sinus seeker" instrument to atraumatically probe and/or investigate anatomical regions in a patient's head. In some versions, ball tip (732) has an outer diameter that is greater than the inner diameter of the lumen of guide catheter (720), such that ball tip (732) is prevented from being pulled proximally into distal end (722) of guide catheter (720).

In the present example, guidewire (730) is coupled with an actuator (712) of handle assembly (710), such that actuator (712) may be translated relative to handle assembly (710) to thereby translate guidewire (730) relative to guide catheter (720). This may enable the operator to selectively translate guidewire (730) between a proximal position (in which ball tip (732) is in contact with distal end (722) of guide catheter (720)) and various distal positions (in which ball tip (732) is spaced distally from distal end (722) of guide catheter (720)). It should also be understood that an actuator (712) may include a rotating element to further provide selective rotation of guidewire (730), about the longitudinal axis of guidewire (730), relative to guide catheter (720). By way of example only, one or more actuators (712) that are associated with guidewire (730) may be provided in accordance with at least some of the teachings of U.S. Pub. No. 2012/0071856, entitled "Medical Device and Method for Treatment of a Sinus Opening," published Mar. 22, 2012, now U.S. Pat. No. 9,554,817, issued Jan. 31, 2017, the disclosure of which is incorporated by reference herein. Likewise, various other features of instrument (700) may be constructed and operable in accordance with at least some of the teachings of U.S. Pub. No. 2012/0071856, now U.S. Pat. No. 9,554,817, issued Jan. 31, 2017.

Dilation catheter (740) is positioned coaxially relative to guide catheter (720) such that dilation catheter (740) wraps around guide catheter (720) like a sheath. As can best be seen in FIG. 12, dilation catheter (740) comprises a catheter portion (742), a balloon dilator (744), and two retaining rings (746) that are positioned on each end of balloon dilator (744). Catheter portion (742) extends distally from handle (710), through balloon dilator (744), and terminates at an open distal end (743) positioned distally of balloon dilator (744). Catheter portion (742) defines a lumen (not shown) that permits guide catheter (720) to extend through the length of catheter portion (742). Catheter portion (742) also provides an inflation lumen (not shown) in fluid communication with balloon dilator (744), such that the inflation lumen may be used to inflate balloon dilator (744) as will be described in greater detail below. At least part of catheter portion (742) is flexible in the present example, such that catheter portion (742) may be translated relative to guide catheter (720) to selectively drive balloon dilator (744) between a proximal position (where balloon dilator (744) is positioned along and/or proximal to curved portion (724)) and a distal position (where balloon dilator (744) is positioned along and/or distal to curved portion (724)). In the present example, one of the actuators (712) of handle (710) is operable to translate dilation catheter (740) relative to guide catheter (720). By way of example only, one or more actuators (712) that are associated with dilation catheter (740) may be provided in accordance with at least some of the teachings of U.S. Pub. No. 2012/0071856, entitled "Medical Device and Method for Treatment of a Sinus Opening," published Mar. 22, 2012, now U.S. Pat. No. 9,554,817, issued Jan. 31, 2017, the disclosure of which is incorporated by reference herein. It should also be understood that handle (710) may include an actuator (712) or other feature that enables the operator to rotate dilation catheter (740) about the longitudinal axis of guide catheter (720), thereby enabling the operator to selectively position balloon dilator (744) at a desired angular position about the longitudinal axis of guide catheter (720).

Balloon dilator (744) is positioned about catheter portion (742) near the open distal end (743) of catheter portion (742). Balloon dilator (744) is comprised of a semi-compliant material in the present example. In some other versions, balloon dilator (744) may be compliant or non-compliant and may comprise any other suitable material such as polyamid (Nylon), polyurethane, polydimethyl siloxane (Silicone), polyester, polyolefin, etc. Various suitable materials and combinations of materials that may be used to form balloon dilator (744) will be apparent to those of ordinary skill in the art in view of the teachings herein.

Figure 15:
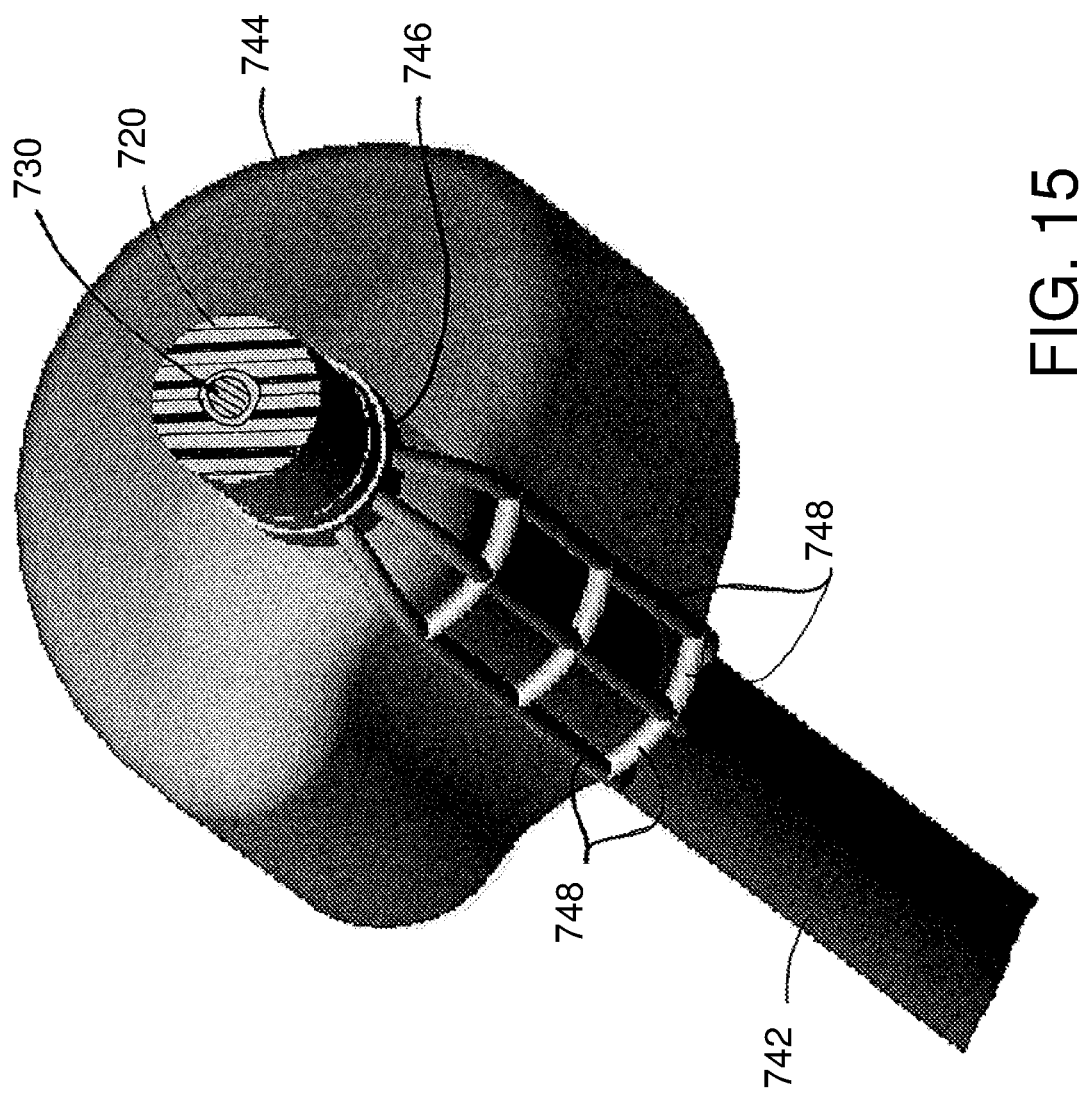
FIG. 15 depicts a perspective view of the distal end of dilation device of FIG. 11, with the balloon in a distally positioned and inflated state.
Figure 16:
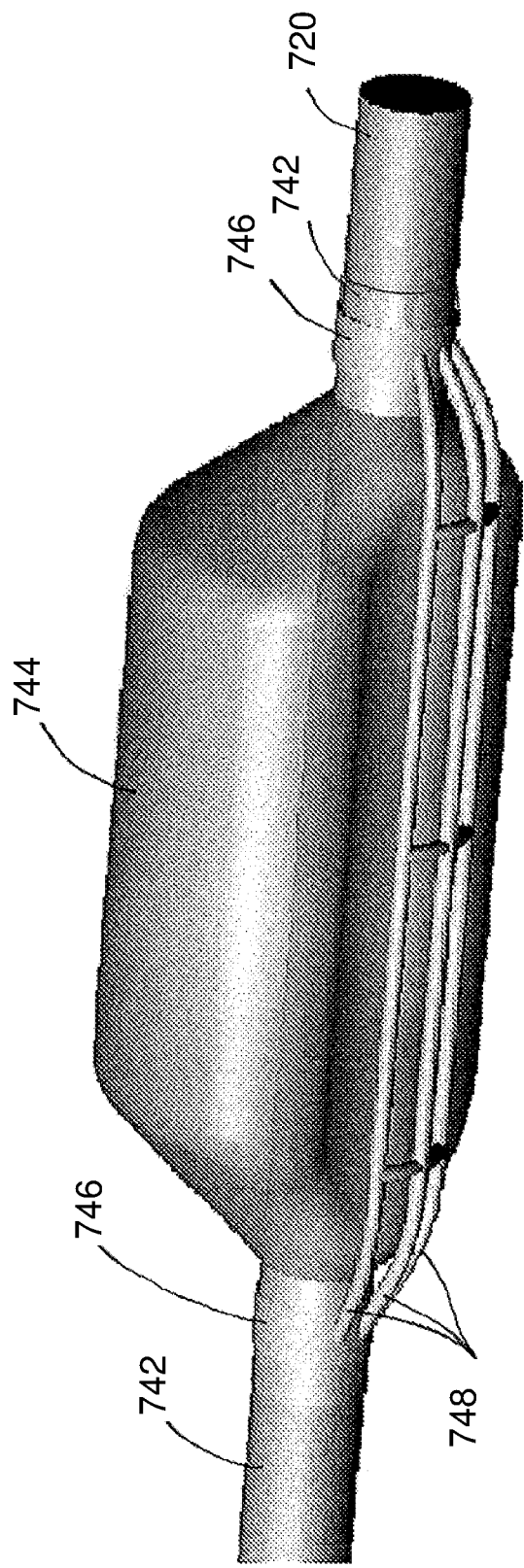
FIG. 16 depicts a side elevational view of the dilation device of FIG. 11, with the balloon in a distally positioned and inflated state.

Retaining rings (746) are positioned at each end of balloon dilator (744) and completely encircle catheter portion (742) and each end of balloon dilator (744). In the present example, retaining rings (746) are fixedly secured to balloon dilator (744). In some other versions, retaining rings (746) may be at least partially slidable relative to balloon dilator (744) and/or catheter portion (742). Retaining rings (746) are connected to each other by a plurality of inelastic retaining wires (748) that extend from one retaining ring (746) to the other. Retaining wires (748) may be grouped together to restrict the inflation of balloon dilator (744) in a given lateral direction, as will be described in greater detail below. As can be seen in FIGS. 15 and 16, retaining wires (748) are connected to each other to form a web-like configuration. In other words, retaining wires (748) are arranged such that there are a plurality (e.g., three) of longitudinally extending retaining wires (748) and a plurality (e.g., three) of transversely extending retaining wires (748). The transversely extending retaining wires (748) are secured to the longitudinally extending retaining wires (748). Such a web-like configuration may maintain retaining wires (748) in a fixed relationship relative to each other or at least restrict the degree to which the longitudinally extending retaining wires (748) may laterally separate from each other. Although a particular fixed relationship is shown, it should be understood that retaining wires (748) may be arranged in any suitable manner. It should also be understood that connections between retaining wires (748) may be omitted such that retaining wires are independent of each other.

In the present example, both retaining rings (746) and retaining wires (748) are comprised of a metallic material such that they may be welded together. In some other versions, retaining rings (746) and retaining wires (748) may be comprised of a polymer or other plastic and are fused or otherwise bonded together (e.g., with an adhesive, etc.). It should also be understood that retaining rings (746) and retaining wires (748) may be dissimilar materials. Of course, retaining rings (746) and retaining wires (748) may be of any other suitable material and may be combined by any other suitable means as will be apparent to those of ordinary skill in the art in view of the teachings herein. In some versions, retaining wires (748) are laterally flexible yet longitudinally inelastic such that the length of each retaining wire (748) is fixed. In some other versions, retaining wires (748) are rigid. In either case, retaining wires (748) cooperate with retaining rings (746) to restrict inflation of balloon dilator (744) on the side of balloon dilator (744) at which wires (748) are positioned. Balloon dilator (744) thus has a constrained side (or region) and an non-constrained side (or region), such that balloon dilator (744) will inflate asymmetrically about the longitudinal axis of dilation catheter (740). In other words, wires (748) constrains expansion of balloon dilator (744) to only a restricted angular range (i.e., less than 360°) about the longitudinal axis of guide catheter (720).

Various other suitable forms that retaining wires (748) may take, as well as various other suitable properties retaining wires (748) may have, will be apparent to those of ordinary skill in the art in view of the teachings herein. It should also be understood that wires (748) are just one example. Any other suitable kinds of structures may be used to constrain expansion of balloon dilator (744) on one side of balloon dilator (744).

Figure 11:
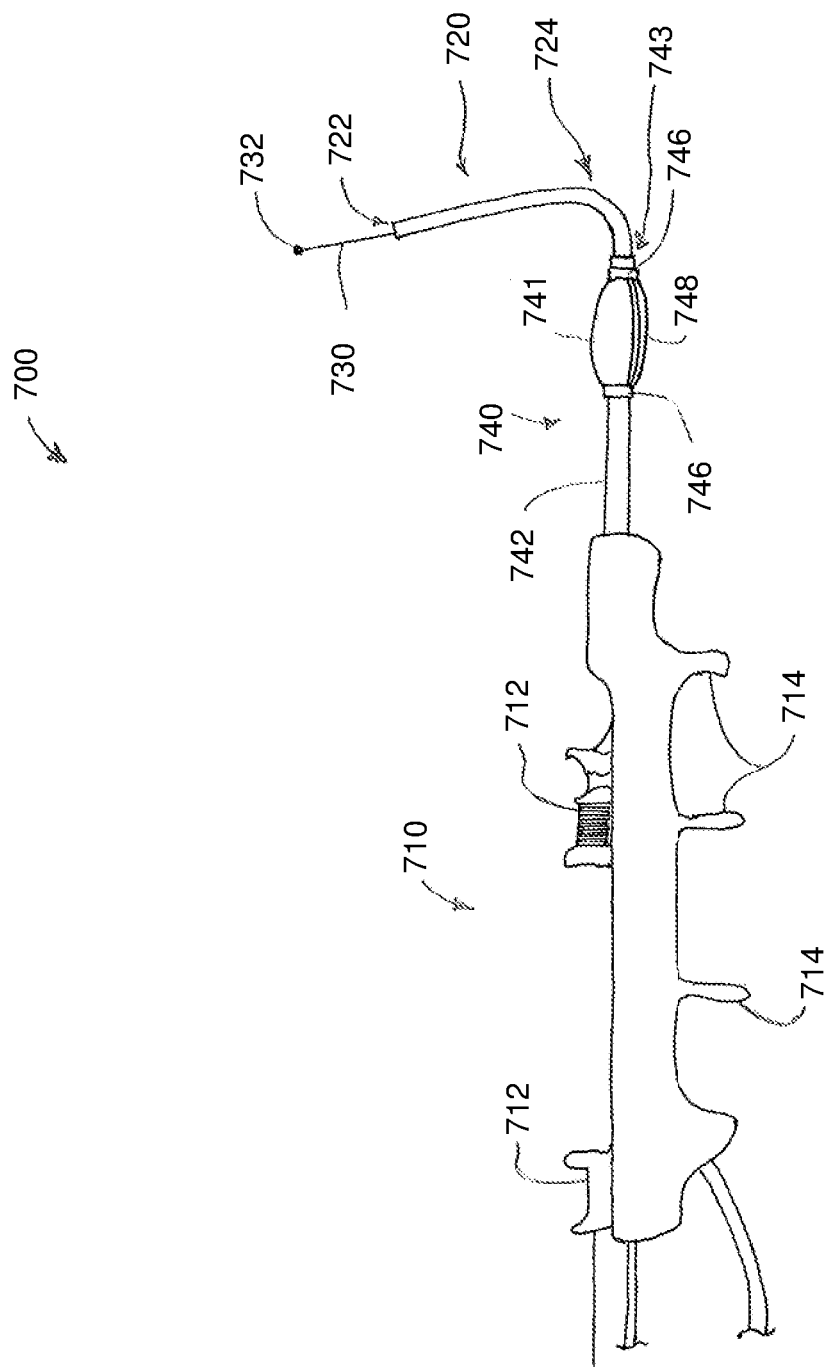
FIG. 11 depicts a side elevational view of an exemplary dilation device with an asymmetric sinus dilation balloon.
Figure 12:
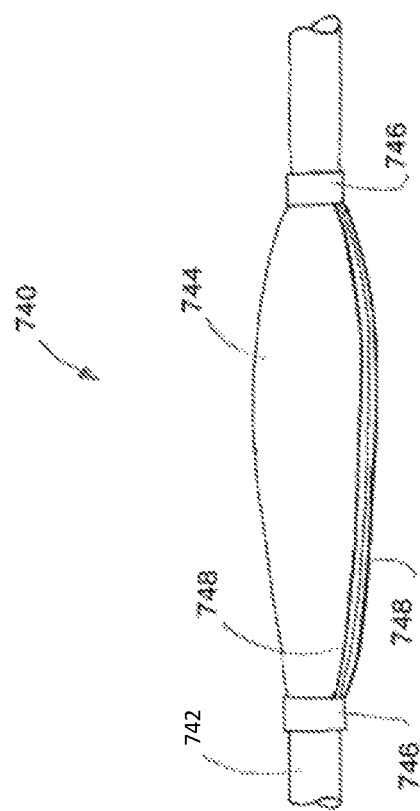
FIG. 12 depicts a detailed side elevational view of the asymmetric sinus dilation balloon of FIG. 11, with the balloon in a non-inflated state.
Figure 13:
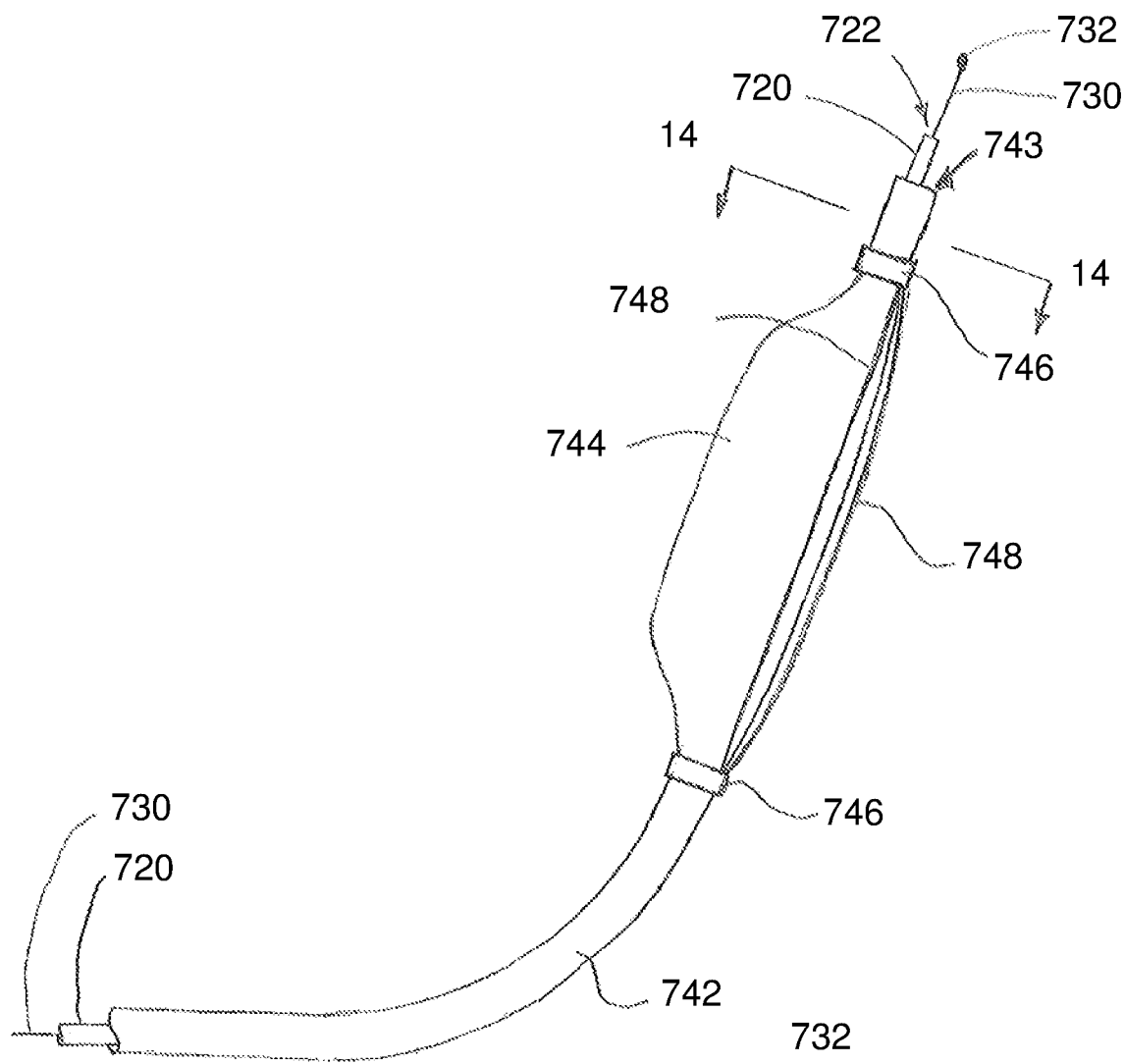
FIG. 13 depicts a detailed side elevational view of the distal end of the dilation device of FIG. 11, with the balloon in a distally positioned and inflated state.
Figure 14:
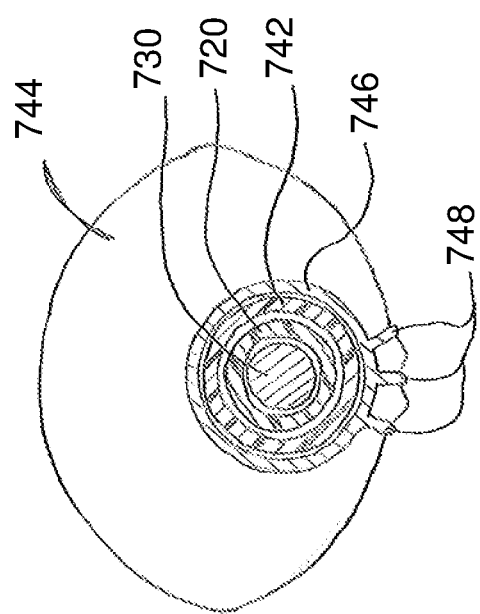
FIG. 14 depicts a cross-sectional view of the dilation device of FIG. 11, with the balloon in a distally positioned and inflated state, the cross-section taken along line 14-14 of FIG. 13.

In an exemplary use, dilation instrument (700) is initially positioned such that open distal end (722) of guide catheter (720) is located within the desired anatomical region while dilation catheter (740) is in a retracted position and non-inflated state shown in FIG. 11. By way of example only, dilation instrument (700) may be positioned such that open distal end (722) of guide catheter (720) is located within the frontal recess, near an agger nasi air cell and suprabullar air cell. Such positioning of the guide catheter (720) may be accomplished using transillumination provided by guidewire (730). In addition or in the alternative, ball tip (732) may be positioned at or distal to distal end (722) of guide catheter (720) such that guide catheter (720) may be used as a seeker tip. Of course, in either case endoscopic visualization may be used to assist with positioning of guide catheter (720).

Once guide catheter (720) is positioned at the desired position within the patient, dilation catheter (740) is advanced distally along guide catheter (720) until balloon dilator (744) is positioned adjacent to the structure that is to be dilated. Catheter portion (742) and balloon dilator (744) are compliant enough to traverse curved portion (724) of guide catheter (720). In one merely illustrative example, balloon dilator (744) may be positioned adjacent to an agger nasi air cell and an suprabullar air cell. Of course, balloon dilator (744) may be positioned in any desired position as will be apparent to those of ordinary skill in the art in view of the teachings herein. It should also be understood that some versions may permit rotation of dilation catheter (740) about guide catheter (720), such that the non-constrained side of balloon dilator (744) may be selectively located at a desired angular position about the longitudinal axis of guide catheter (720).

After dilation catheter (740) has been advanced to a suitable distal position, fluid (e.g., saline) is then communicated through the inflation lumen to inflate balloon dilator (744) to the inflated state shown in FIGS. 13-16. As can be seen, rigid wires (748) are configured to prevent the expansion of balloon dilator (744) in a particular direction or range of directions. Rigid wires (748) further act to transfer force from the restricted side of balloon dilator (744) to handle (710) via guide catheter (720) such that an operator may direct the force of expansion toward a structure that is intended to be remodeled. Thus, the expansion of balloon dilator (744) may reconstruct one anatomical structure while leaving another adjacent anatomical structure unaffected. For instance, when balloon dilator (744) is positioned within the frontal recess, with the expanding portion of balloon dilator (744) anterior to the frontal recess, balloon dilator (744) may reconstruct the agger nasi air cell while leaving an adjacent suprabullar air cell intact. Alternatively, dilation instrument (700) (or dilation catheter (740)) may be rotated 180° such that the expanding portion of balloon dilator (744) is posterior to the frontal recess to reconstruct the suprabullar air cell while leaving the adjacent agger nasi air cell intact. In other words, balloon dilator (744) is configured to selectively apply a force to an anatomical structure on one side of balloon dilator (744) while not applying force to the anatomical structure on the other side of balloon dilator (744).

In some versions, dilation instrument (700) may include other structures that may be used to assist in mechanically grounding handle (710) such that the expansion of balloon dilator (744) causes remodeling of only the anatomical structure that is on the expandable side of balloon dilator (744). In other words, mechanical grounding may prevent the expansion of balloon dilator (744) from remodeling the anatomical structure that is on the same side of balloon dilator (744) as wires (748) (i.e., the constrained side of balloon dilator (744)). Such mechanical grounding may, for example, include an external structure that is mounted to a patient table, a procedure chair, or any other suitable structure.

As noted above, dilation instrument (700) may be used in various other procedures and in various other parts of a patient's anatomy (e.g., in some other outflow tract of a patient's paranasal sinus). In addition to having dilation catheter (740) positioned at any suitable angular orientation about the longitudinal axis of guide catheter (720), it should be understood that balloon dilator (744) may be advanced to (and dilated at) any suitable location along the length of guide catheter (720). In other words, in some uses dilation catheter (740) stops advancing at curved portion (724) or proximal to curved portion (724), with balloon dilator (744) then being inflated at that point. In some alternative versions of dilation instrument (700), dilation catheter (740) does not translate along guide catheter (720) and is simply fixed in position at the distal end of guide catheter (720). Various other suitable ways in which dilation instrument (700) may be configured and used will be apparent to those of ordinary skill in the art in view of the teachings herein.

IV. Exemplary Support for Uncinate Process

As noted above, dilation instruments (80, 100, 700) may be used to dilate the ethmoid infundibulum (EI) by moving the uncinate process (UP), to dilate the frontal recess (FR), and/or to dilate other anatomical structures. In some instances, this process may effectively remodel the uncinate process (UP) and/or other anatomical structure(s) such that the ethmoid infundibulum (EI) remains dilated for at least a desired period of time. However, the uncinate process (UP) and/or other anatomical structure(s) may eventually move back to a previous position and/or other conditions may eventually arise where the ethmoid infundibulum (EI) is no longer effectively dilated. This may or may not be undesirable. In instances where it is desirable to maintain dilation of the ethmoid infundibulum (EI), one or more implantable devices may be installed at or near the ethmoid infundibulum (EI) to maintain the dilated state. Various examples of such implantable devices are described in greater detail below while others will be apparent to those of ordinary skill in the art in view of the teachings herein. It should be understood that the implantable devices described below may be used after either of the dilation instruments (80, 100, 700) described above have been used to dilate the ethmoid infundibulum (EI); or after some other instrument has been used to dilate the ethmoid infundibulum (EI). Furthermore, various suitable ways in which the implantable devices described below may be positioned and installed will be apparent to those of ordinary skill in the art in view of the teachings herein. For instance, any of the below described implantable devices may be installed using visualization from endoscope (60) or some other form of visualization. It should also be understood that, while the examples described below are provided in the context of the ethmoid infundibulum (EI), the devices and techniques described below may be readily adapted for use in various other parts of a patient's anatomy.

Figure 17:
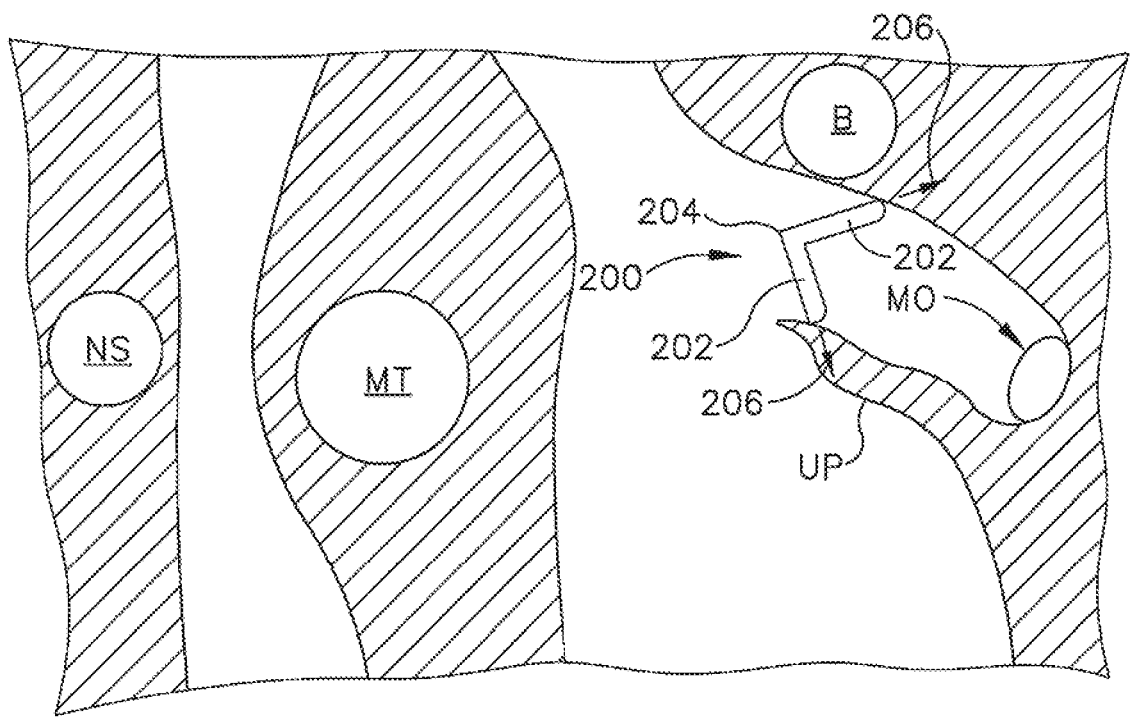
FIG. 17 depicts a coronal cross-sectional view of the portion of the nasal cavity depicted in FIG. 6, with an exemplary uncinate process support positioned to maintain the uncinate process in the remodeled position of FIG. 8B.

FIG. 17 shows an exemplary wedge (200) that may be used to maintain dilation of the ethmoid infundibulum (EI). Wedge (200) of this example comprises a pair of legs (202) that are joined together at a vertex (204), thereby forming a wedge angle. In the present example, wedge (200) is oriented such that vertex (204) points generally medially toward the middle turbinate (MT). In some other versions, wedge (200) is oriented such that vertex (204) points toward the maxillary ostium (MO). Alternatively, wedge (200) may be positioned such that vertex (204) points anteriorly, posteriorly, superiorly, inferiorily, or any suitable combination thereof. The free end of each leg (202) includes a respective barbed anchor (206). As shown, one anchor (206) is secured in the ethmoid bulla (B) in this example while the other anchor is secured in the uncinate process (UP). Alternatively, anchors (206) may be secured elsewhere. As yet another merely illustrative variation, vertex (204) may include an anchor in addition to or in lieu of legs (202) having anchors (206). By way of example only, vertex (204) may have an anchor that is secured in the middle turbinate (MT). Other suitable arrangements will be apparent to those of ordinary skill in the art in view of the teachings herein.

Wedge (200) may be formed of a rigid material. Alternatively, wedge (200) may be formed of a malleable material. As yet another merely illustrative alternative, wedge (200) may be formed of a resilient material that is biased to assume a position like the one shown in FIG. 17; yet that compresses to facilitate insertion of wedge (200) into the final installation position. In still other versions, wedge (200) is formed by a pair of rigid legs that pivot at or near vertex (204). For instance, a mechanical hinge or a living hinge may be located at or near vertex (204). Such a hinge may be resiliently biased or may be selectively locked/unlocked to enable installation of wedge (200). It should be understood that wedge (200) may be installed at any suitable position along the length of the uncinate process (UP), and that the configuration of wedge (200) should not obstruct the fluid path through the ethmoid infundibulum (EI). It should also be understood that wedge (200) may be formed of a bioabsorbable material, if desired. By way of example only, wedge (200) may be formed of polylactic acid (PLA), polydioxanone (PDS), polycaprolactone, and/or any other suitable material(s).

Figure 18:
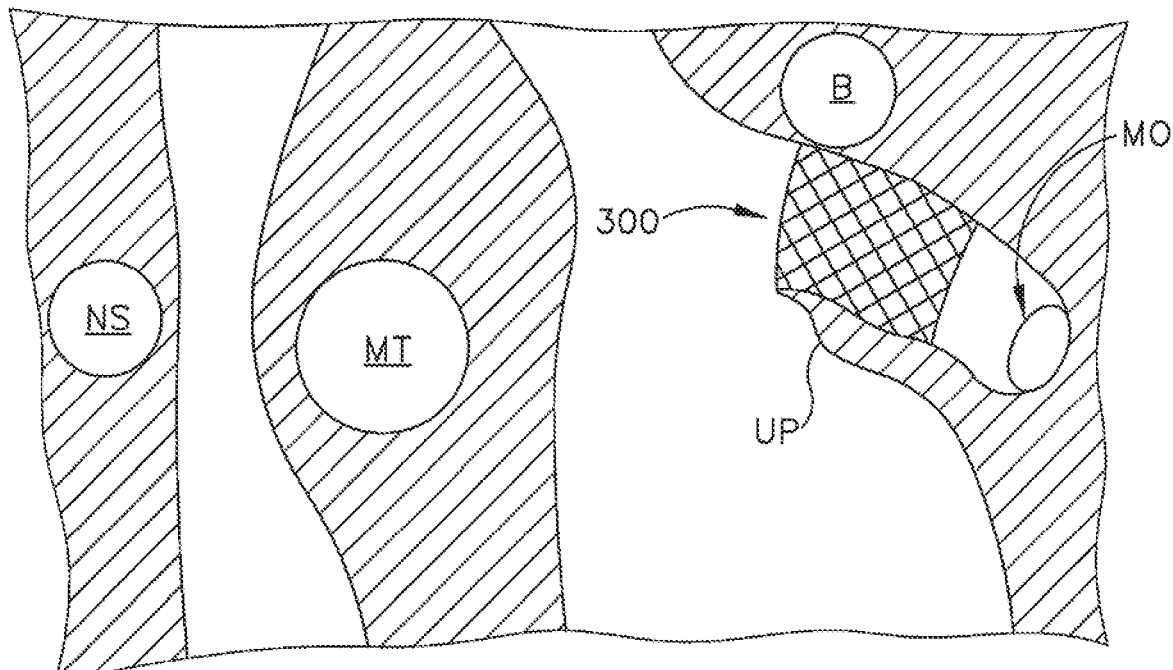
FIG. 18 depicts a coronal cross-sectional view of the portion of the nasal cavity depicted in FIG. 6, with another exemplary uncinate process support positioned to maintain the uncinate process in the remodeled position of FIG. 8B.

FIG. 18 shows an exemplary mesh scaffold (300) that may be in used to maintain dilation of the ethmoid infundibulum (EI). Scaffold (300) may be installed within the ethmoid infundibulum (EI) such that scaffold (300) is interposed between the ethmoid bulla (B) and the uncinate process (UP). In some versions, scaffold (300) is formed of a resilient material (e.g., nitinol, etc.), such that scaffold (300) is held in a compressed state until it reaches the installation site where it is then released to expand outwardly. This outward bias of scaffold (300) may both hold the ethmoid infundibulum (EI) in the dilated state and effectively secure scaffold to the ethmoid bulla (B) and the uncinate process (UP) (e.g., due to mucosa tissue protruding through the openings defined between the wires forming the mesh of scaffold (300), etc.). In some other versions, scaffold (300) is malleable such that scaffold (300) is actively expanded to reach the state shown in FIG. 18. By way of example only, scaffold (300) may be positioned about the exterior of a dilator while scaffold is in a non-expanded state and while the dilator is in the non-inflated state. The dilator and scaffold (300) may then be positioned in the ethmoid infundibulum (EI), wherein the dilator may then be inflated to dilate the ethmoid infundibulum (EI). Scaffold (300) may expand with the dilator in the ethmoid infundibulum (EI). The dilator may then be deflated and removed from the patient, leaving scaffold (300) in place in an expanded state within the ethmoid infundibulum (EI). Other suitable configurations, properties, and installation techniques for scaffold (300) will be apparent to those of ordinary skill in the art in view of the teachings herein.

Figure 19:
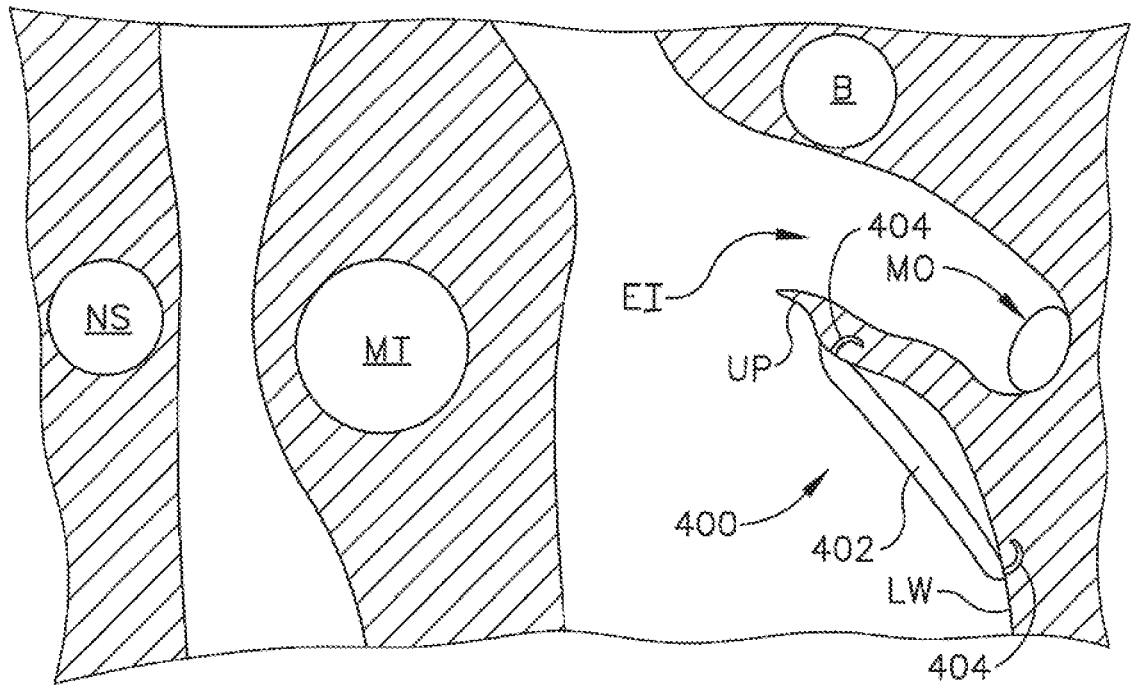
FIG. 19 depicts a coronal cross-sectional view of the portion of the nasal cavity depicted in FIG. 6, with another exemplary uncinate process support positioned to maintain the uncinate process in the remodeled position of FIG. 8B.

FIG. 19 shows an exemplary tether (400) that may be used to maintain dilation of the ethmoid infundibulum (EI). Tether (400) of this example comprises an elongate body (402) that has hook anchors (404) at each end. One hook anchor (404) is secured to the inferior side of the uncinate process (UP) while the other hook anchor (404) is secured to the medial side of the lateral wall (LW). Tether body (402) is configured to maintain tension between anchors (404), thereby holding the uncinate process (UP) in the position shown in FIG. 19, to thereby maintain dilation of the ethmoid infundibulum (EI). By way of example only, tether (400) may comprise polyester or some other biocompatible textile that does not stretch. As another merely illustrative example, tether (400) may comprise a metal and/or plastic material. Other suitable materials and configurations that may be incorporated into tether (400) will be apparent to those of ordinary skill in the art in view of the teachings herein.

In some instances, tether (400) is installed while a separate dilator is used to move and temporarily hold the uncinate process (UP) into the position shown in FIG. 19. In some other instances, tether (400) is used to move the uncinate process (UP) into the position shown in FIG. 19. For instance, a hook anchor (404) may first be secured in the inferior side of the uncinate process (UP) or on any other region of the uncinate process (UP). The operator may then pull on tether body (402) to move the uncinate process (UP) medially and/or anteriorly. While holding the moved position of the uncinate process (UP), the operator may then secure the other hook anchor (404) the medial side of the lateral wall (LW). Other suitable ways in which tether (400) may be installed will be apparent to those of ordinary skill in the art in view of the teachings herein.

Figure 20:
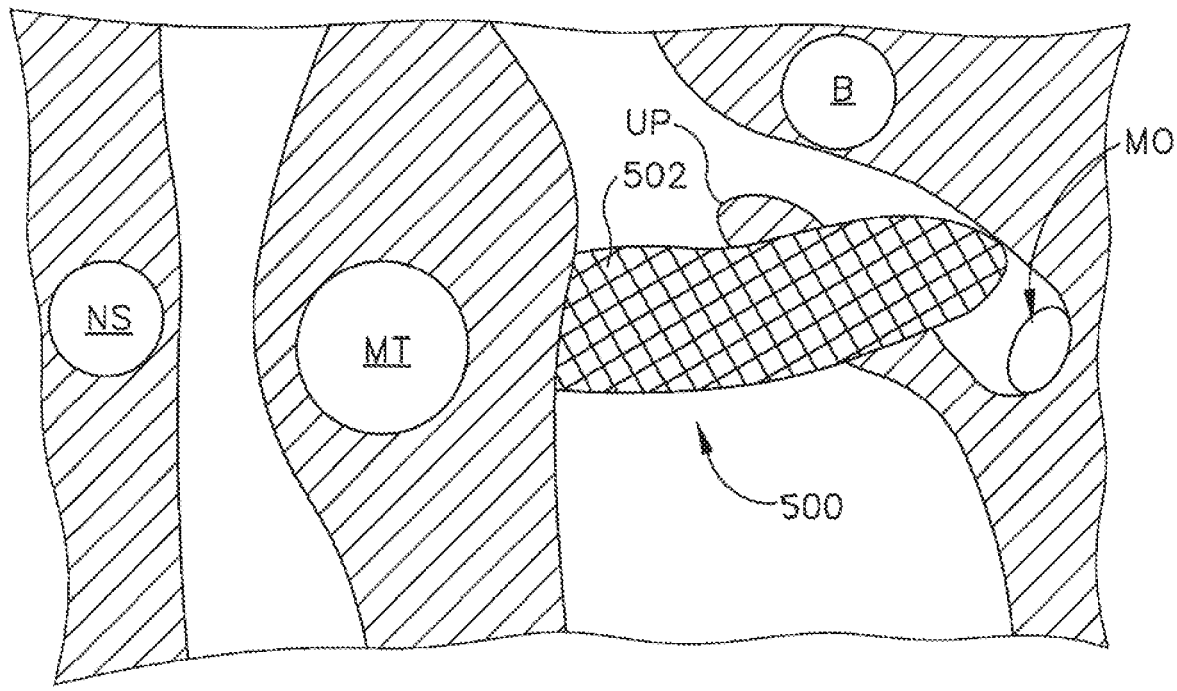
FIG. 20 depicts a coronal cross-sectional view of the portion of the nasal cavity depicted in FIG. 6, with another exemplary uncinate process support positioned to maintain the uncinate process in the remodeled position of FIG. 8B.

FIG. 20 shows another exemplary positioning device (500) that may be used to maintain dilation of the ethmoid infundibulum (EI). Device (500) is configured for installation in a position where device (500) will bear medially on the middle turbinate (MT) while bearing anteriorly on the uncinate process (UP). Device (500) of this example comprises a resilient mesh body (502). It should be understood that a mesh is just one example, and that any other suitable kind of structure may be used to form body (502). It should also be understood that body (502) may be malleable instead of being resilient. Other suitable configurations and properties for device (500) will be apparent to those of ordinary skill in the art in view of the teachings herein. Similarly, various suitable ways in which device (500) may be installed will be apparent to those of ordinary skill in the art in view of the teachings herein.

V. Exemplary Infundibular Illumination Device

As noted above, the natural anatomy of the ethmoid infundibulum (EI) may make it difficult to access the maxillary ostium (MO). The anatomy of the ethmoid infundibulum (EI) may also make it difficult to effectively illuminate and visualize the ethmoid infundibulum (EI) (e.g., to thereby visualize the maxillary ostium (MO)). By way of example only, it may be desirable to illuminate and visualize the ethmoid infundibulum (EI) and maxillary ostium (MO) in order to gauge the location, irritation, size, and other characteristics of the maxillary ostium (MO). It may also be desirable to illuminate and visualize the ethmoid infundibulum (EI) and maxillary ostium (MO) in order to position dilation catheter system (10) or some other device to dilate the maxillary ostium (MO). Furthermore, it may be desirable to illuminate and visualize the ethmoid infundibulum (EI) to search for pouches, dead ends, tissue qualities that could influence a therapeutic decision, etc., within the ethmoid infundibulum (EI) itself.

The anatomy of some patients may enable illumination/viewing of the ethmoid infundibulum (EI) (and perhaps even the maxillary ostium (MO)) simply using an apparatus such as endoscope (60) described above. However, in some other patients, endoscope (60) may not provide sufficient illumination/visualization of the ethmoid infundibulum (EI) and/or the maxillary ostium (MO). It may therefore be desirable to provide an additional illumination and/or visualization device that provides enhanced illumination/viewing capabilities within the ethmoid infundibulum (EI). Examples of such devices are described in greater detail below, while still other examples will be apparent to those of ordinary skill in the art in view of the teachings herein. While the exemplary devices are described in the context of illuminating/viewing the ethmoid infundibulum (EI), it should be understood the devices described below may be readily used in various other regions of the nasal cavity.

Figure 21A:
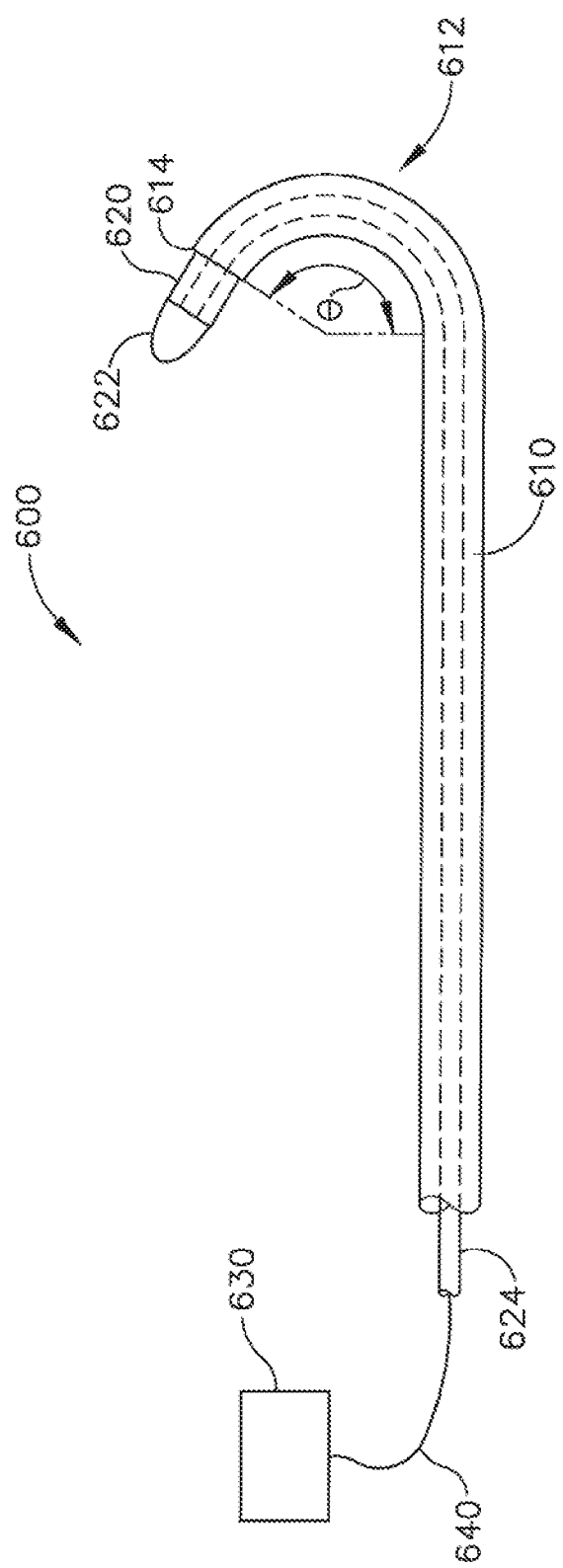
FIG. 21A depicts a side elevational view of an exemplary infundibular illuminating device, with an illuminating wire in a retracted position.
Figure 21B:
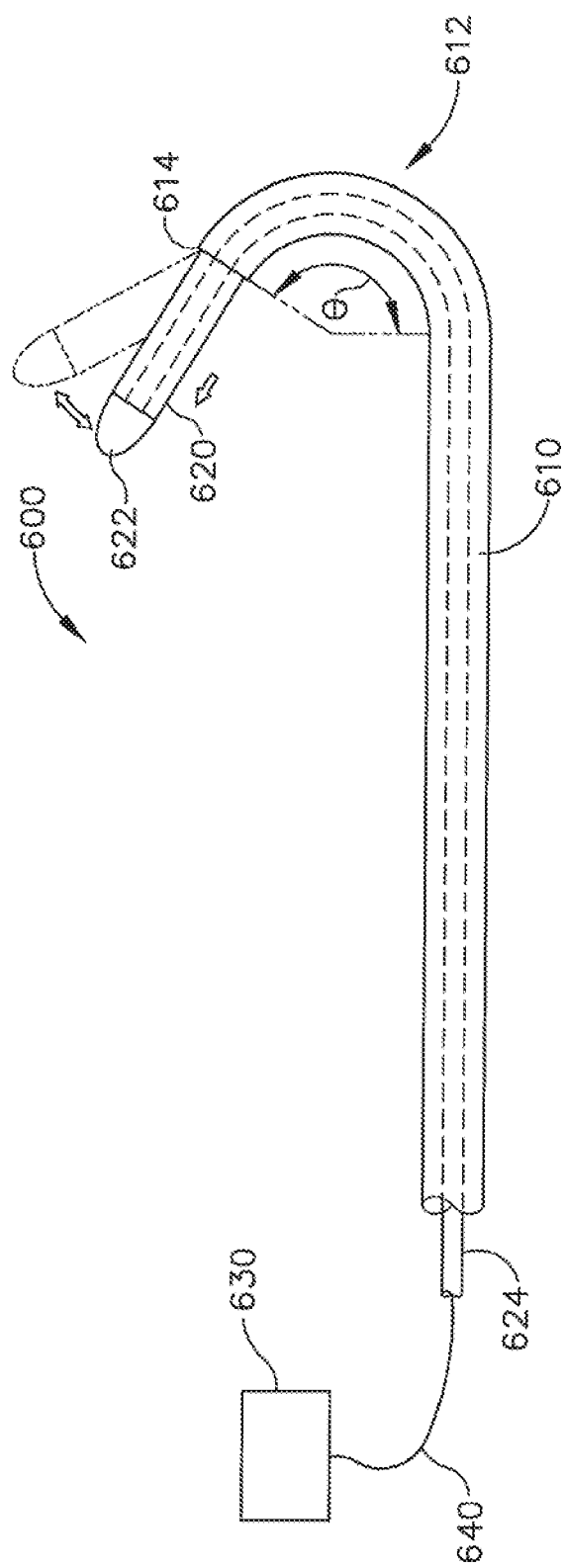
FIG. 21B depicts a side elevational view of the infundibular illuminating device of FIG. 21A, with the illuminating wire in an extended position.

FIGS. 21A-21B show an exemplary infundibular illuminator (600) that is operable to illuminate the ethmoid infundibulum (EI). Illuminator (600) of this example comprises an outer tube (610) and an inner tube (620) that is slidably disposed in outer tube (610). Outer tube (610) is formed of a rigid or semi-rigid material (e.g., a metal, plastic, and/or other material). Outer tube (610) has a radiused curved region (612) that terminates in distal end (614). In the present example, curved region (612) is defined by a constant radius sweeping along an arc angle (Θ-theta), beginning at the proximal portion of curved region (612) and ending at distal end (614). In some versions, the arc angle (Θ-theta) is at least 90 degrees. In some such versions, the arc angle (Θ-theta) is at least 135 degrees. In some such versions, the arc angle (Θ-theta) is at least 180 degrees. Curved region (612) may be rigid, semi-rigid, or resilient. For instance, at least a portion of curved region (612) may be resiliently biased to assume the position shown in FIG. 21A.

Inner tube (620) has a distal tip (622) and at least one internal optical fiber (624). Distal tip (622) of the present example has a wedge-like profile but is atraumatic. Thus, when distal tip (622) is advanced into a narrowly defined ethmoid infundibulum (EI), distal tip (622) may assist in driving the ethmoid bulla (B) and uncinate process (UP) apart without causing damage to either anatomical structure. In some instances, illuminator (600) is used in conjunction with one of the support devices discussed above for maintaining dilation of the ethmoid infundibulum (EI), such that tip (622) may not need to drive apart the ethmoid bulla (B) and uncinate process (UP). Optical fiber (624) extends along the length of inner tube (620) and is coupled with a light source (630) via an optical cable (640). Light source (630) may comprise a conventional external light source. In some other versions, light source (630) is integrated into illuminator (600). In some such versions, illuminator (600) also includes an integral power source (e.g., a battery) to power light source (630). Light source (630) may comprise an LED, laser, or any other suitable source of light. Light source (630) may also be configured to generate light having a specific wavelength associated with specific types of normal and/or diseased tissue, such that the light from light source (630) will make such tissue visibly stand out.

Cable (640) and fiber (624) are configured to transmit light from light source (630) to tip (622). Tip (622) comprises a transparent or translucent material that is configured to project light from fiber (624). Thus, tip (622) may illuminate the ethmoid infundibulum (EI) when tip (622) is positioned within the ethmoid infundibulum (EI). In addition to tip (622) providing illumination, other portions of inner tube (620) may also provide illumination. For instance, inner tube (620) may include a plurality of transversely extending light pipes located proximal to tip (622).

With outer tube (610) being held in position, inner tube (620) may be advanced distally relative to outer tube (610) (as shown in FIG. 21B) to extend tip (622) further into the ethmoid infundibulum (EI), thereby illuminating further depths of the ethmoid infundibulum (EI). In addition, inner tube (620) of the present example is steerable, such that the portion of inner tube (620) extending distal to distal end (614) may be selectively deflected away from an axis that is perpendicular to the opening defined by distal end (614). This may further enhance control of illumination by illuminator (600) within the ethmoid infundibulum (EI). Various suitable features that may be used to provide advancement of inner tube (620) relative to outer tube (610) will be apparent to those of ordinary skill in the art in view of the teachings herein. Similarly, various suitable features that may be used to provide deflection of inner tube (620) away from an axis that is perpendicular to the opening defined by distal end (614) will be apparent to those of ordinary skill in the art in view of the teachings herein. It should be noted that advaceability and steerability of inner tube (620) are merely optional. For instance, some versions of illuminator (600) may lack inner tube (620), such that tip (622) is unitary with distal end (614) of outer tube (610). In addition, some versions of inner tube (620) may be advanceable but not steerable. As yet another merely illustrative variation, a light emitting feature within inner tube (620) may be steerable while inner tube (620) itself is not steerable. For instance, a light emitting feature within inner tube (620) may be pivotable within inner tube (620).

It should be understood that curved region (612) may enable illuminator (600) to be used as a retractor. By way of example only, illuminator (600) may be positioned such that tip (622) is used to initially drive the ethmoid bulla (B) and uncinate process (UP) apart. With tip (622) positioned within the ethmoid infundibulum (EI), and with curved region (612) engaging the uncinate process (UP), illuminator (600) may be gently pulled inferiorly to displace the uncinate process (UP) and open the ethmoid infundibulum (EI) wider. Illuminator (600) may thus be used as an uncinate process (UP) retractor. Outer tube (610) may include a soft outer material (e.g., rubber, foam, etc.) to minimize trauma to the uncinate process (UP) when illuminator (600) is used as a retractor. While using outer tube (610) to hold the uncinate process (UP) in a retracted position, the operator may manipulate tip (622) to illuminate the ethmoid infundibulum (EI). The combination of uncinate process (UP) retraction and ethmoid infundibulum (EI) illumination provided by illuminator (600) may greatly enhance visualization of the ethmoid infundibulum (EI). In some instances, this may enable the operator to view the ethmoid infundibulum (EI) (and in some cases the maxillary ostium (MO)) using endoscope (60) while using illuminator (600) as a retractor and as a source of light. It should also be understood that illuminator (600) may itself include an optical assembly that enables viewing through illuminator (600). Various other suitable components, configurations, and methods of operating illuminator (600) will be apparent to those of ordinary skill in the art in view of the teachings herein.

VI. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) a guide member, wherein the guide member defines a longitudinal axis;
(b) an expandable dilator operable to expand from a collapsed state to an expanded state, wherein the expandable dilator is configured to slide along a path defined by the guide member; and
(c) a constraining member, wherein the constraining member is positioned and configured to engage a side portion of the expandable dilator as the expandable dilator transitions to the expanded state, and thereby cause asymmetrical expansion of the expandable dilator relative to the longitudinal axis of the guide member, wherein the constraining member comprises:
(i) a first end element,
(ii) a second end element spaced longitudinally apart from the first element, wherein the first and second end elements encircle the guide member, and
(iii) a medial element extending longitudinally between and secured to the first and second end elements, wherein the medial element directly contacts the expandable dilator.

2. The apparatus of claim 1, wherein the expandable dilator comprises an inflatable dilator, wherein the apparatus further comprises an inflation lumen in fluid communication with the inflatable dilator.

3. The apparatus of claim 1, wherein the guide member comprises a rail.

4. The apparatus of claim 3, wherein the rail includes a longitudinally extending track.

5. The apparatus of claim 4, wherein the constraining member includes a key element configured to slide longitudinally within the longitudinally extending track.

6. The apparatus of claim 1, wherein the constraining member is configured to engage the side portion of the expandable dilator to thereby restrict expansion of the expandable dilator in a direction toward the longitudinal axis.

7. The apparatus of claim 1, wherein the expandable dilator is coupled to the constraining member such that a constrained side of the expandable dilator and a non-constrained side of the expandable dilator are both arranged on the same lateral side of the guide member.

8. The apparatus of claim 1, wherein the medial element comprises a platform arranged outwardly of the guide member, wherein the expandable dilator is coupled to the platform.

9. The apparatus of claim 8, wherein the first and second end elements are configured to slide longitudinally along the guide member.

10. The apparatus of claim 1, wherein the guide member comprises a catheter.

11. The apparatus of claim 1, wherein the constraining member is configured to permit the expandable dilator to expand in a first radial direction by a first radial distance, and in an opposite second radial direction by a second radial distance, wherein the first radial distance is less than the second radial distance.

12. The apparatus of claim 1, wherein the medial element comprises at least one wire.

13. The apparatus of claim 12, wherein the at least one wire comprises a plurality of longitudinally extending wires and at least one laterally extending wire that connects the longitudinally extending wires.

14. The apparatus of claim 12, wherein the first end element comprises a first ring arranged at a first end of the expandable dilator, and the second end element comprises a second ring arranged at a second end of the expandable dilator, wherein the at least one wire connects the first ring with the second ring.

15. The apparatus of claim 1, wherein the guide member includes a ball tip.

16. An apparatus comprising:
(a) a guide member, wherein the guide member defines a longitudinal axis;
(b) an expandable dilator operable to expand from a collapsed state to an expanded state, wherein the expandable dilator is configured to slide along a path defined by the guide member; and
(c) a constraining member, wherein the constraining member is positioned and configured to restrict expansion of the expandable dilator in a first radial direction while permitting expansion of the expandable dilator in a second radial direction opposite the first radial direction, wherein the constraining member comprises at least one wire that extends longitudinally along an outer surface of the expandable dilator.

17. The apparatus of claim 16, wherein the expandable dilator comprises an inflatable dilator, wherein the apparatus further comprises an inflation lumen in fluid communication with the inflatable dilator.

18. The apparatus of claim 16, wherein the expandable dilator includes a constrained side configured to engage the constraining member, and a non-constrained side configured to expand without engaging the constraining member, wherein the constrained side and the non-constrained side are arranged on the same lateral side of the guide member.

19. An apparatus comprising:
(a) a guide member defining a longitudinal axis, wherein an exterior of the guide member includes a longitudinally extending track; and
(b) a dilation assembly slidable relative to the guide member, wherein the dilation assembly comprises:
(i) a sliding structure coupled to the guide member and having a constraining portion, wherein the sliding structure is configured to slide longitudinally along the track along the exterior of the guide member, and
(ii) an expandable dilator coupled with the sliding structure, wherein the expandable dilator is operable to expand from a collapsed state to an expanded state,
wherein the constraining portion of the sliding structure is configured to abut a side portion of the expandable dilator to thereby restrict expansion of the expandable dilator in a direction toward the longitudinal axis,
wherein the track is configured to maintain an angular orientation of the dilation assembly about the longitudinal axis relative to the guide member.

20. The apparatus of claim 19, wherein the constraining portion extends along an exterior of the guide member.

* * * * *